United States Patent
Wakazome

(10) Patent No.: US 11,602,259 B2
(45) Date of Patent: Mar. 14, 2023

(54) IMAGE PROCESSING APPARATUS, DISPLAY SYSTEM IMAGE PROCESSING METHOD, AND STORAGE MEDIUM THAT PROCESSES AN IMAGE OF DENTITION INCLUDING A PLURALITY OF TEETH IN AN ORAL CAVITY

(71) Applicant: J. MORITA MFG. CORP., Kyoto (JP)

(72) Inventor: Naonori Wakazome, Kyoto (JP)

(73) Assignee: J. MORITA MFG. CORP., Kyoto (JP)

( * ) Notice: Subject to any disclaimer, the term of this patent is extended or adjusted under 35 U.S.C. 154(b) by 268 days.

(21) Appl. No.: 16/822,444

(22) Filed: Mar. 18, 2020

(65) Prior Publication Data
US 2020/0297187 A1 Sep. 24, 2020

(30) Foreign Application Priority Data

Mar. 18, 2019 (JP) .............................. JP2019-049942

(51) Int. Cl.
*A61B 1/00* (2006.01)
*A61B 1/24* (2006.01)
(Continued)

(52) U.S. Cl.
CPC ............ *A61B 1/00045* (2013.01); *A61B 1/24* (2013.01); *G06T 5/005* (2013.01); *G06T 5/50* (2013.01); *G06T 19/20* (2013.01); *G06T 2207/20084* (2013.01); *G06T 2207/20092* (2013.01); *G06T 2207/20212* (2013.01); *G06T 2207/30036* (2013.01); *G06T 2219/2004* (2013.01)

(58) Field of Classification Search
CPC ... G06T 19/003; G06T 2200/04; G06T 15/00; G06T 2207/30036; G06T 2210/41; G06T 17/00
See application file for complete search history.

(56) References Cited

U.S. PATENT DOCUMENTS

| 6,227,850 B1 * | 5/2001 | Chishti ................... A61C 7/00 433/213 |
| 9,329,675 B2 | 5/2016 | Ojelund et al. |

(Continued)

FOREIGN PATENT DOCUMENTS

| JP | 2000-155788 A | 6/2000 |
| JP | 2002-291694 A | 10/2002 |

(Continued)

OTHER PUBLICATIONS

Imburgia et al. "Accuracy of four intraoral scanners in oral implantology: a comparative in vitro study" BMC Oral Health; London, UK; Jun. 2, 2017 (13 pages).

(Continued)

*Primary Examiner* — Guillermo M Rivera-Martinez
(74) *Attorney, Agent, or Firm* — Osha Bergman Watanabe & Burton LLP

(57) ABSTRACT

An image processing apparatus includes an acquisition unit that acquires three-dimensional data of dentition including a plurality of teeth in an oral cavity, a generator that generates multi-image data of a plurality of images different in point of view toward the dentition based on the three-dimensional data acquired by the acquisition unit, and an output unit that outputs the multi-image data generated by the generator to a display.

27 Claims, 19 Drawing Sheets

(51) Int. Cl.
*G06T 5/00* (2006.01)
*G06T 5/50* (2006.01)
*G06T 19/20* (2011.01)

(56) References Cited

U.S. PATENT DOCUMENTS

| | | | |
|---|---|---|---|
| 9,607,383 B2 | 3/2017 | Adamson | |
| 10,039,475 B2 | 8/2018 | Sorimoto et al. | |
| 10,383,549 B2 | 8/2019 | Sorimoto et al. | |
| 2005/0043837 A1* | 2/2005 | Rubbert | A61C 7/00 700/118 |
| 2005/0287492 A1* | 12/2005 | Lazzarato | A61C 13/0004 433/173 |
| 2006/0212260 A1* | 9/2006 | Kopelman | G16Z 99/00 702/152 |
| 2007/0238065 A1* | 10/2007 | Sherwood | A61C 7/08 433/24 |
| 2008/0057466 A1* | 3/2008 | Jordan | A61C 9/0046 433/69 |
| 2008/0170238 A1* | 7/2008 | Ochi | G01B 11/25 356/610 |
| 2010/0215220 A1* | 8/2010 | Yamaguchi | G06T 7/246 382/106 |
| 2010/0283781 A1* | 11/2010 | Kriveshko | G06T 17/00 715/849 |
| 2013/0108981 A1* | 5/2013 | Duret | A61B 5/1077 433/29 |
| 2013/0162645 A1* | 6/2013 | Ulrici | A61B 6/14 345/424 |
| 2013/0209954 A1 | 8/2013 | Prakash et al. | |
| 2013/0257718 A1* | 10/2013 | Ojelund | A61B 5/0088 345/156 |
| 2013/0286174 A1* | 10/2013 | Urakabe | A61B 1/247 348/66 |
| 2015/0002509 A1* | 1/2015 | Rohaly | H04N 13/00 345/420 |
| 2015/0156461 A1* | 6/2015 | Jessop | H04N 7/18 348/47 |
| 2015/0206306 A1 | 7/2015 | Adamson | |
| 2015/0296184 A1* | 10/2015 | Lindenberg | H04N 7/18 348/77 |
| 2015/0305696 A1* | 10/2015 | Yamakawa | A61B 6/466 378/19 |
| 2017/0202483 A1 | 7/2017 | Sorimoto et al. | |
| 2017/0281110 A1* | 10/2017 | Mandelkern | A61B 6/5217 |
| 2017/0367789 A1 | 12/2017 | Fujiwara et al. | |
| 2018/0028063 A1* | 2/2018 | Elbaz | G06T 7/75 |
| 2018/0109727 A1 | 4/2018 | Tamai et al. | |
| 2018/0168781 A1* | 6/2018 | Kopelman | A61B 90/36 |
| 2018/0192964 A1* | 7/2018 | Stalder | A61B 5/6886 |
| 2018/0206959 A1* | 7/2018 | Ohtake | G06T 7/66 |
| 2018/0296131 A1* | 10/2018 | Kaji | A61B 5/1079 |
| 2018/0325425 A1 | 11/2018 | Sorimoto et al. | |
| 2019/0073924 A1* | 3/2019 | Biemans | G06F 3/0346 |
| 2019/0125493 A1* | 5/2019 | Salah | A61C 7/002 |
| 2019/0231491 A1* | 8/2019 | Sabina | A61B 5/0086 |
| 2021/0174543 A1* | 6/2021 | Claessen | G06T 17/20 |

FOREIGN PATENT DOCUMENTS

| | | |
|---|---|---|
| JP | 2010-533549 A | 10/2010 |
| JP | 2012-139540 A | 7/2012 |
| JP | 2013-192773 A | 9/2013 |
| JP | 2015-524724 A | 8/2015 |
| JP | 2016-174903 A | 10/2016 |
| JP | 2017-020930 A | 1/2017 |
| JP | 2018-527965 A | 9/2018 |
| WO | 2004/028391 A2 | 4/2004 |
| WO | 2004/028391 A3 | 6/2004 |
| WO | 2009/011959 A1 | 1/2009 |
| WO | 2013/141404 A1 | 9/2013 |
| WO | 2016/143022 A1 | 9/2016 |
| WO | 2016/199735 A1 | 12/2016 |
| WO | 2017/111116 A1 | 6/2017 |

OTHER PUBLICATIONS

Medina-Sotomayor et al. "Relationship between resolution and accuracy of four intraoral scanners in complete-arch impressions" Journal of Clinical and Experimental Dentistry; Jan. 1, 2018 (6 pages).
Extended European Search Report issued in European Application No. 20163535.6, dated Sep. 28, 2020 (18 pages).
"Maestro 3D Ortho Studio: Innovative solutions for orthodontic applications" Retrieved from the Internet: URL: https://web.archive.org/web/20130919063447if/http://www.turkuazdental.com:80/download/pdf/orthostudio_presentation.pdf; Sep. 19, 2013 (16 pages).
Exocad GmbH "exocad DentalCAD 2.3 Metera with Smile Creator add-on module" Retrieved from the Internet: URL: https://www.youtube.com/watch?v=QWJA52 A57aY ; Mar. 12, 2019 (2 pages).
J. H. Noar et al. "A discerning approach to simple aesthetic orthodontics" British Dental Journal, vol. 218, No. 3; Feb. 1, 2015 (10 pages).
Partial European Search Report issued in European Application No. 20163535.6, dated Jul. 9, 2020 (17 pages).
Office Action issued in the counterpart Japanese Patent Application No. 2019-049942, dated May 25, 2021 (10 pages).

* cited by examiner

| MANNER OF REPRESENTATION OF IMAGE | CONTENT |
|---|---|
| SUPPLEMENTAL IMAGE 312 | SUPPLEMENTED PORTION |
| URGING IMAGE 314 | URGING PORTION |
| TRANSPARENT REGION 316 | MISSING PORTION |

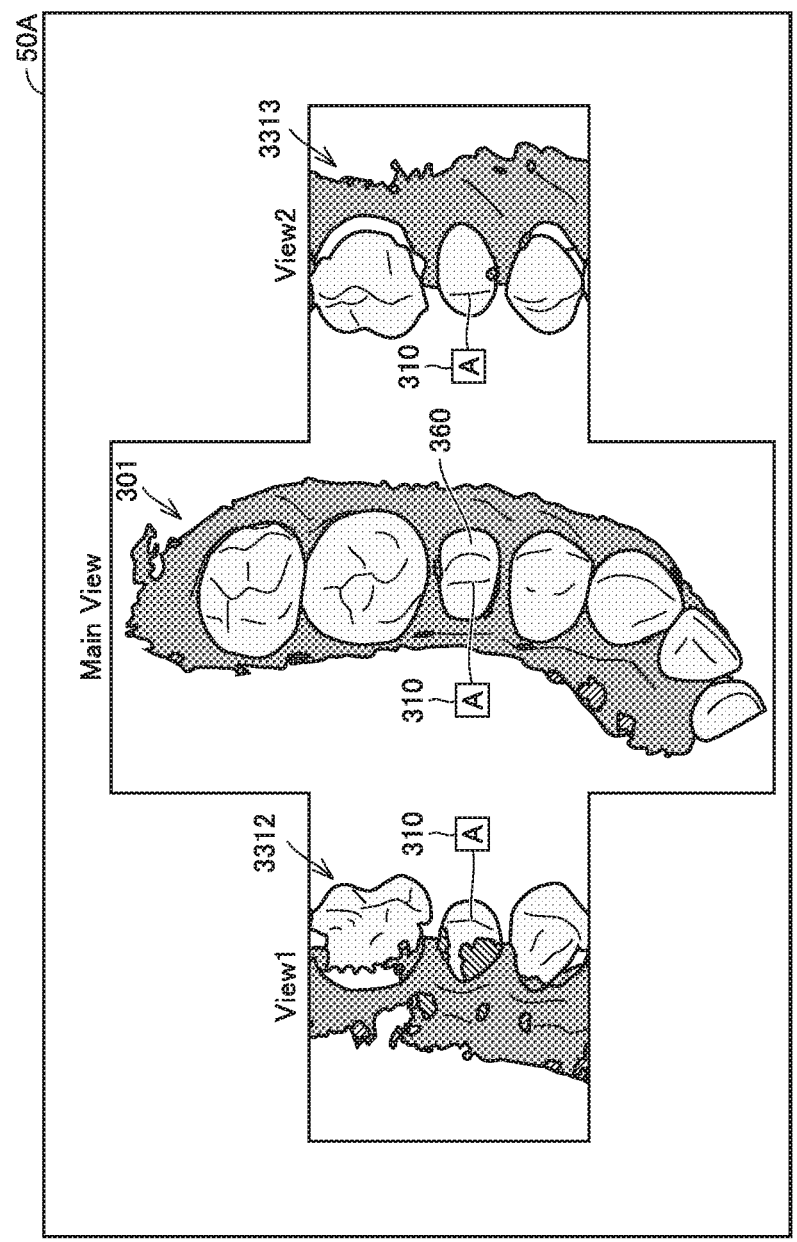

FIG.19
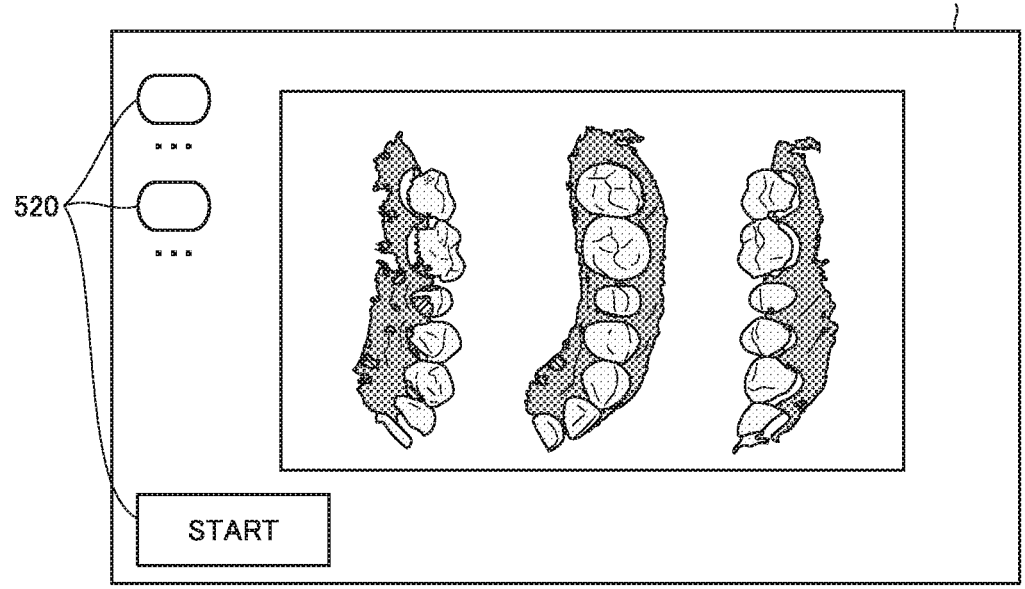
(A) FIRST REPRESENTATION STATE
(LOW-MAGNIFICATION REPRESENTATION STATE)
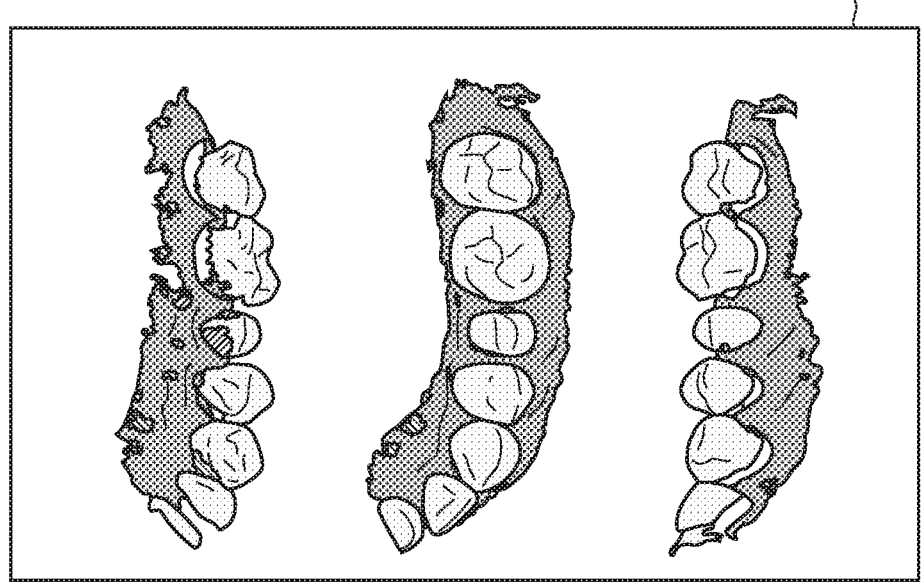
(B) SECOND REPRESENTATION STATE
(HIGH-MAGNIFICATION REPRESENTATION STATE)

FIRST DISPLAY

SECOND DISPLAY

IMAGE PROCESSING APPARATUS, DISPLAY SYSTEM IMAGE PROCESSING METHOD, AND STORAGE MEDIUM THAT PROCESSES AN IMAGE OF DENTITION INCLUDING A PLURALITY OF TEETH IN AN ORAL CAVITY

BACKGROUND OF THE INVENTION

Field of the Invention

The present invention relates to an image processing apparatus, a display system, an image processing method, and a storage medium that stores an image processing program and particularly to an image processing apparatus that processes an image of dentition including a plurality of teeth in an oral cavity, a display system that shows the image, an image processing method of processing the image, and a storage medium that stores a program for processing the image.

Description of the Background Art

A technique for scanning dentition in an oral cavity with a three-dimensional scanner and showing an image of the three-dimensionally scanned dentition on a display apparatus has conventionally been proposed. For example, Japanese Patent Laying-Open No. 2017-20930 has proposed a technique for showing an image of dentition on a display apparatus for allowing a user to recognize to which extent dentition image has been scanned.

SUMMARY OF THE INVENTION

A user may desire to perform, during scanning of dentition in the oral cavity, checking processing for checking whether or not there is a portion that has not completely been scanned. According to the technique described in Japanese Patent Laying-Open No. 2017-20930, only a dentition image from one point of view has been shown during scanning. Therefore, in order to perform checking processing with other points of view being included, a mouse or the like should be operated to rotate the image of dentition. It is not hygienically preferred, however, that the user touches an external device during scanning. Therefore, in consideration of a hygienic aspect, the user may wear gloves to touch the external device or the external device may be covered with a disposable cover. Use of gloves or a cover, however, disadvantageously leads to increase in time and effort and to lowering in convenience in processing for checking of the dentition image by the user.

The present invention was made to solve the problem above, and an object thereof is to provide an image processing apparatus that improves convenience in processing for checking of a dentition image by a user, a display system, an image processing method, and an image processing program.

An image processing apparatus according to one embodiment includes an acquisition unit that acquires three-dimensional data of dentition including a plurality of teeth in an oral cavity, a generator that generates image data of a plurality of images different in point of view toward the dentition based on the three-dimensional data acquired by the acquisition unit, and an output unit that outputs to the outside, the image data generated by the generator.

According to another aspect, a display system includes a three-dimensional scanner that generates three-dimensional data of dentition including a plurality of teeth in an oral cavity, an image processing apparatus, and a display. The image processing apparatus includes an acquisition unit that acquires the three-dimensional data from the three-dimensional scanner, a generator that generates image data of a plurality of images different in point of view toward the dentition based on the three-dimensional data acquired by the acquisition unit, and an output unit that outputs the image data generated by the generator to the display. The display shows the plurality of images based on the image data output from the output unit.

According to another aspect, an image processing method includes acquiring three-dimensional data of dentition including a plurality of teeth in an oral cavity, generating image data of a plurality of images different in point of view toward the dentition based on the three-dimensional data, and outputting the image data.

According to another aspect, a computer readable storage medium stores a program that causes a computer to perform acquiring three-dimensional data of dentition including a plurality of teeth in an oral cavity, generating image data of a plurality of images different in point of view toward the dentition based on the three-dimensional data, and outputting the image data.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 14 shows an exemplary picture shown on the display in a second embodiment.

FIG. 19 shows an exemplary picture shown on the display in a seventh embodiment.

DESCRIPTION OF PREFERRED EMBODIMENTS

Embodiments according to the present invention will be described below with reference to the drawings.

First Embodiment

[Configuration of Display System 100]

Figure 1:
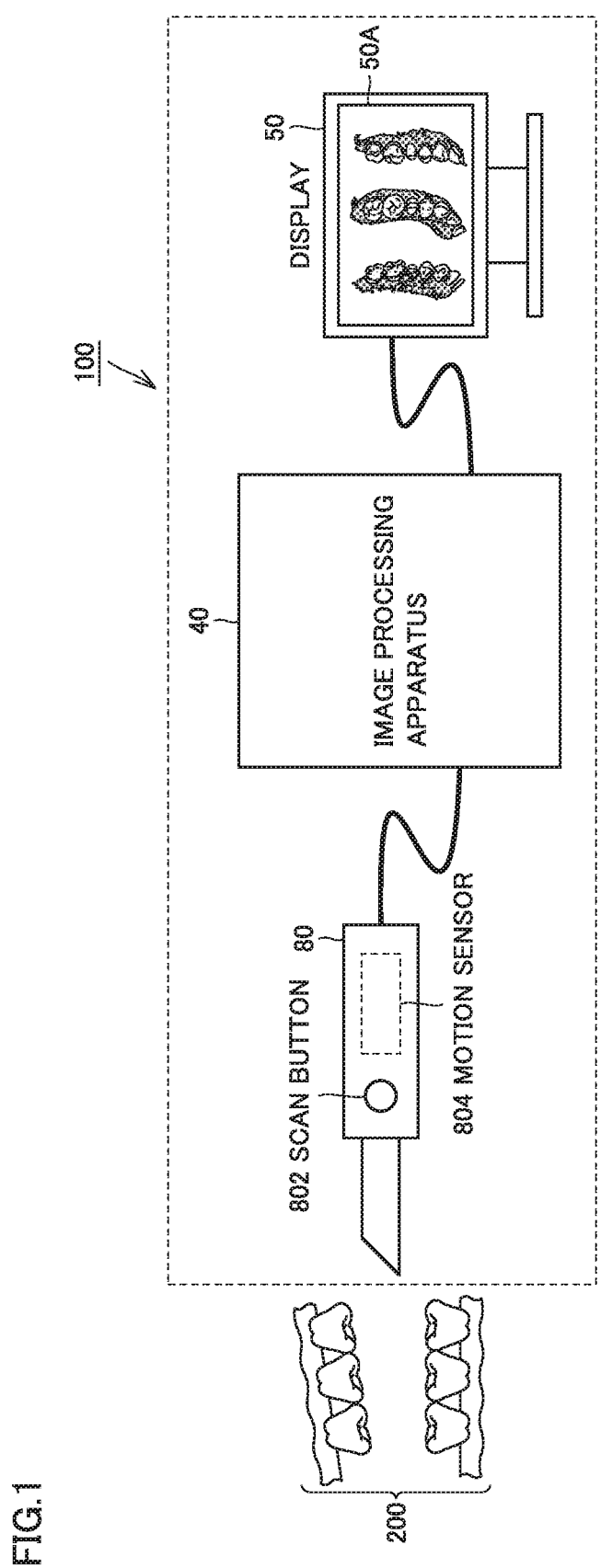
FIG. 1 is a diagram showing an exemplary configuration of a display system according to the present embodiment.

FIG. 1 is a block diagram showing a configuration of a display system 100 according to a first embodiment of the present invention. Display system 100 shown in FIG. 1 includes a three-dimensional scanner 80, an image processing apparatus 40, and a display 50 (which is also referred to as a display apparatus). Three-dimensional scanner 80 and image processing apparatus 40 are connected to each other through a wire or wirelessly. Three-dimensional scanner 80 and display 50 are connected to each other through a wire or wirelessly.

A user (operator) inserts three-dimensional scanner 80 into an oral cavity. Three-dimensional scanner 80 acquires three-dimensional data of an object by an operation by the user. In other words, three-dimensional scanner 80 picks up an image of the object each time an extremely short time period T (for example, 0.1 second) elapses. Three-dimensional scanner 80 acquires three-dimensional data by image pick-up each time it picks up an image. Three-dimensional scanner 80 transmits the acquired three-dimensional data to image processing apparatus 40.

In the present embodiment, dentition 200 and gingiva in the oral cavity are defined as an "object". Description will be given below with dentition 200 and gingiva being defined as the object. Three-dimensional data includes coordinate information and color information associated with the coordinate information. The coordinate information includes, for example, an X-axis coordinate, a Y-axis coordinate, and a Z-axis coordinate. The color information includes, for example, RGB information.

Though not shown, three-dimensional scanner 80 includes an optical component (a pattern generation element) that generates a pattern to be projected on dentition 200 and a light source, a lens component that forms an image of the pattern on a surface of dentition 200, a focus varying unit that can vary a focal position, and an optical sensor (a CCD image sensor or a CMOS image sensor) that picks up an image of the projected pattern. Three-dimensional scanner 80 may acquire a three-dimensional shape in accordance with principles of a focus method. Alternatively, three-dimensional scanner 80 may acquire a three-dimensional shape in accordance, for example, with principles of a confocal point method. Three-dimensional scanner 80 may be configured in accordance with any principles so long as it acquires a three-dimensional shape with an optical approach.

Figure 3:
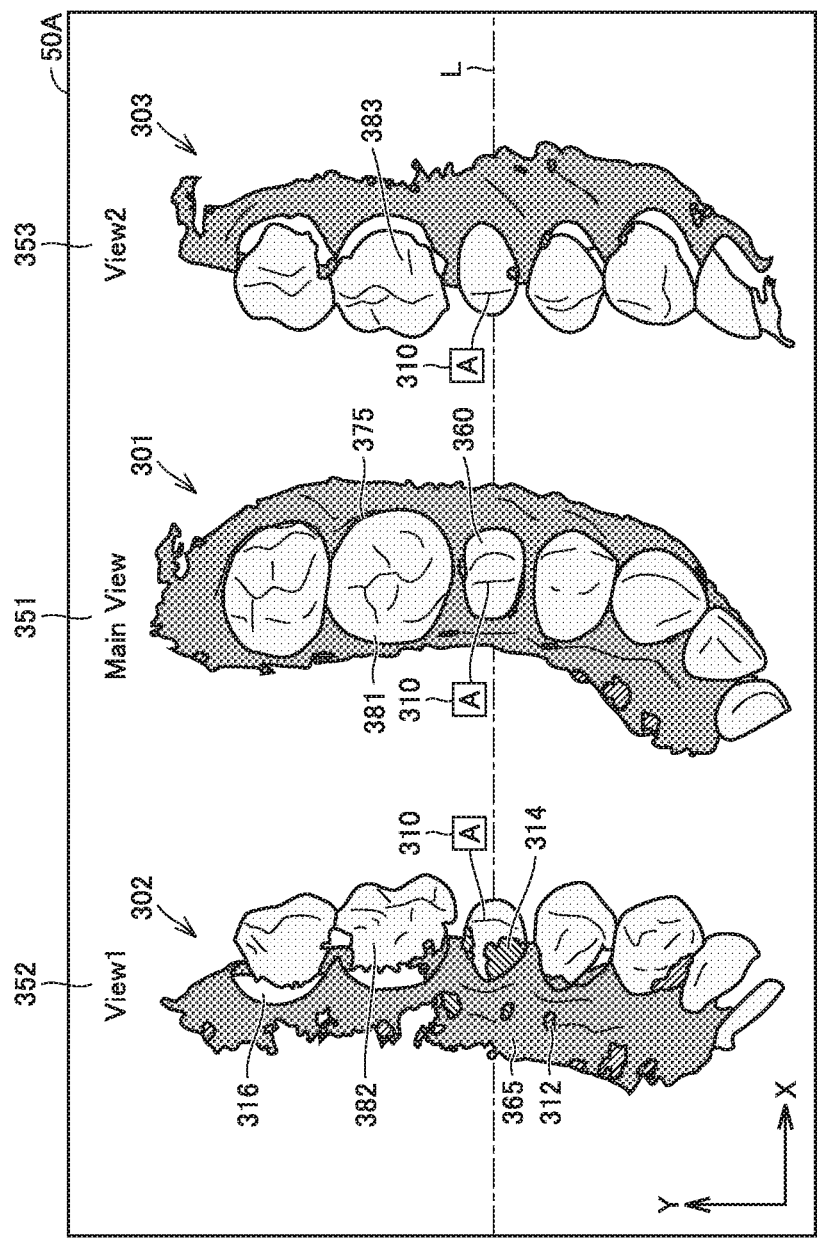
FIG. 3 shows exemplary representation on the display in the present embodiment.
Figures 4, 5:
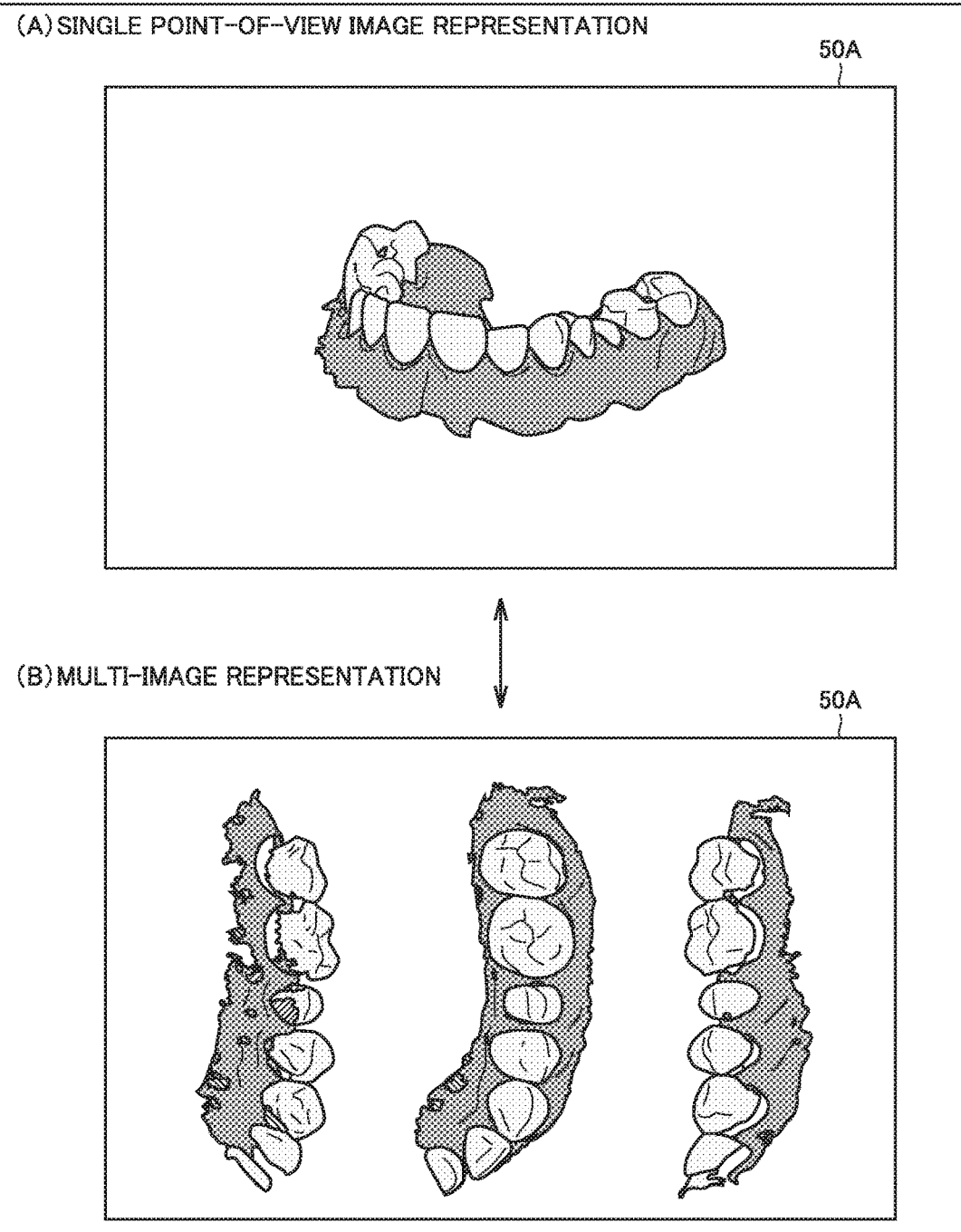
FIG. 4 is a diagram showing correspondence between a manner of representation of an image and a content of the manner.
FIG. 5 is a diagram showing an exemplary image shown on the display in the present embodiment.

A scan button 802 is arranged on the outside of three-dimensional scanner 80. Scan button 802 is a button operable by a user. A user can perform various operations onto scan button 802. The various operations include a first operation, a second operation, and a third operation below. For example, a short press operation is defined as the first operation. A press-and-hold operation is defined as the second operation. Two consecutive operations (double click) are defined as the third operation. For example, the first operation is an operation to start a scan mode in which three-dimensional data is acquired by successive shooting of an object by three-dimensional scanner 80. The first operation is also an operation to stop the scan mode during the scan mode. The second operation is an operation to cause image processing apparatus 40 to start a multi-representation mode. The multi-representation mode refers to a mode in which a multi-image created by combination of a plurality of images is shown on display 50 as shown in FIGS. 3 and 5 (B). The third operation is an operation to select a target tooth which will be described later.

Three-dimensional scanner 80 contains a motion sensor 804. Motion sensor 804 detects an operation onto three-dimensional scanner 80 by a user. For example, an acceleration sensor is adopted as motion sensor 804.

Image processing apparatus 40 generates image data by performing image processing onto three-dimensional data transmitted from three-dimensional scanner 80. Image processing apparatus 40 may be implemented, for example, by a general-purpose computer or a computer dedicated for image processing apparatus 40. For example, a personal computer (PC) or a tablet may be adopted as the general-purpose computer. At least a part of operations for generating image data by performing image processing onto three-dimensional data may be performed by software executed by a CPU of image processing apparatus 40 or by hardware that performs processing separately from the CPU.

Image processing apparatus 40 outputs image data to the outside. In the example in FIG. 1, the "outside" means display 50.

Display 50 shows various images under the control by image processing apparatus 40. Typically, display 50 shows in a display area 50A, an image based on image data acquired by image processing apparatus 40. Display 50 shows an image of an object based on three-dimensional data acquired by three-dimensional scanner 80. Display 50 may be implemented by any of a liquid crystal display (LCD), an organic electroluminescence (EL) display, a tablet, smart glasses, a head mounted display, and an aerial display.

An exemplary method of using display system 100 will now briefly be described. A user starts up image processing apparatus 40 by turning on the power (not shown) of image processing apparatus 40. Then, image processing apparatus 40 enters a state that scanning by three-dimensional scanner 80 can be performed based on an operation by a user. Image processing apparatus 40 enters the state that the scanning by three-dimensional scanner 80 can be performed, for example, by launch of a scanning application by a user. Alternatively, image processing apparatus 40 may enter the state that scanning by three-dimensional scanner 80 can be performed, for example, by being connected to a server or a cloud server in a medical facility through a prescribed web browser by an operation by a user. The present embodiment adopts a configuration that image processing apparatus 40 enters the state that scanning by three-dimensional scanner 80 can be performed, for example, by being connected to a server or a cloud server in a medical facility through a prescribed web browser by an operation by a user.

Then, the user designates a patient name saved in the server or the cloud server in the medical facility on a prescribed web browser and designates a scanning icon (not shown) of the application. Then, the user turns on the power of three-dimensional scanner 80. Then, the user wears gloves or the like and inserts three-dimensional scanner 80 into the oral cavity of the patient. Then, as the user performs the second operation onto scan button 802 of three-dimensional scanner 80 in the oral cavity, three-dimensional scanner 80 starts scanning processing. By performing the second operation onto scan button 802 during scanning processing by three-dimensional scanner 80, scanning processing ends (is stopped).

[Content Shown on Display]

Figure 2:
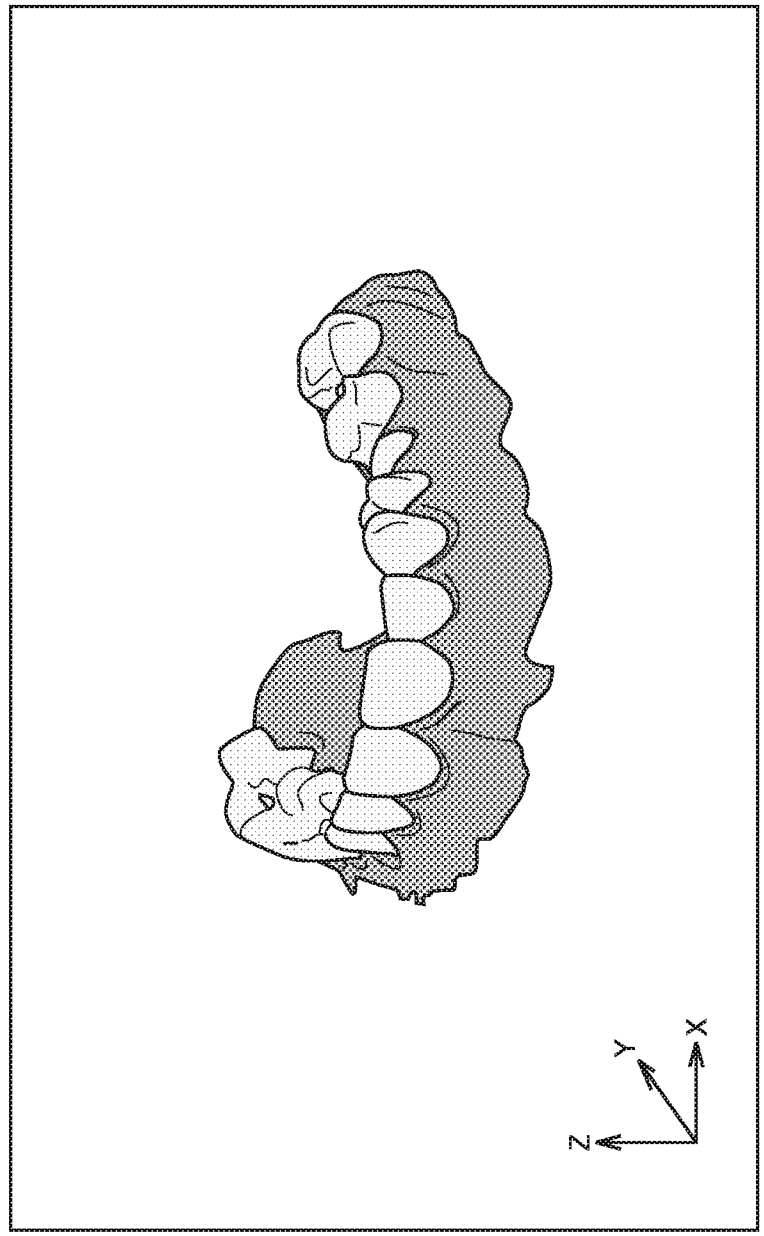
FIG. 2 shows an exemplary image shown on a display in a comparative example.

FIG. 2 shows an exemplary image shown on a display of a display system in a comparative example. As shown in FIG. 2, an axis in a direction of a line that connects a right rearmost molar among teeth in the oral cavity and a left rearmost molar to each other is defined as an "X axis." The X axis points also to a direction of width of the oral cavity. An axis in a direction of height of a tooth is defined as a "Z axis." An axis orthogonal to the X axis and the Z axis is defined as a "Y axis." The Y axis points also to a direction of depth of the oral cavity. Though an image shown on the display in FIG. 2 or subsequent figures shows the X axis, the Y axis, and the Z axis, the display actually does not show the X axis, the Y axis, and the Z axis.

The example in FIG. 2 shows an image of dentition in the mandible. A user may desire to check the shown dentition image for an unscanned portion. The example in FIG. 2 shows only the dentition image from one point of view. Therefore, when the user checks the dentition image for an unscanned portion during scanning of dentition in the oral cavity, the user should operate a mouse (not shown) connected to a display apparatus to rotate the image of the dentition and then check whether or not there is an unscanned portion. It is not hygienically preferred, however, to touch an external device such as a mouse during scanning. In consideration of a hygienic aspect, the user may wear gloves to touch the external device and the external device may be covered with a disposable cover. Use of gloves or a cover, however, disadvantageously leads to increase in time and effort and to lowering in convenience in processing for checking of a dentition image by the user. Increase in cost for gloves or a cover also gives rise to a problem. An image shown in FIG. 2 is also referred to as a "single point-of-view image" below.

FIG. 3 shows exemplary representation on display 50 of display system 100 in the present embodiment. As shown in FIG. 3, display 50 in the present embodiment shows a plurality of images different in point of view toward dentition 200 (a first image 301, a second image 302, and a third image 303 in the example in FIG. 3). Therefore, a user can recognize images when dentition is viewed in a plurality of directions without rotating the shown dentition image, and consequently the user can check the images for an unscanned portion. Since the user thus does not have to operate an external device, the user does not have to wear gloves or a disposable cover does not have to be attached to the external device. As set forth above, according to the present embodiment, convenience in processing for checking of a dentition image by the user can be improved.

Details of FIG. 3 will now be described. First image 301, second image 302, and third image 303 are also collectively referred to as a "multi-image" below. The multi-image in FIG. 3 is an image mainly focusing on right rear molar 375 in dentition 200. In the example in FIG. 3, display 50 shows first image 301, second image 302, and third image 303.

First image 301 is an image showing dentition 200 in a first point-of-view direction (dentition 200 viewed in the first point-of-view direction). Second image 302 is an image showing dentition 200 in a second point-of-view direction (dentition 200 viewed in the second point-of-view direction). Third image 303 is an image showing dentition 200 in a third point-of-view direction (dentition 200 viewed in the third point-of-view direction). The first point-of-view direction, the second point-of-view direction, and the third point-of-view direction correspond to a first point-of-view direction D1, a second point-of-view direction D2, and a third point-of-view direction D3 in FIG. 7, respectively.

The first point-of-view direction (the point-of-view direction in first image 301) is a direction from a point of view toward an occlusal surface 381 of molar 375 or also a direction of height (the Z-axis direction) of molar 375. The second point-of-view direction (the point-of-view direction in second image 302) is a direction from a point of view toward a lingual side surface 382 of molar 375. The third point-of-view direction (the point-of-view direction in second image 303) is a direction from a point of view toward a buccal side surface 383 of molar 375.

In other words, the first point-of-view direction is perpendicular or substantially perpendicular to occlusal surface 381 of molar 375. The second point-of-view direction is perpendicular or substantially perpendicular to the direction of dentition 200 (in the example in FIG. 3, the Y-axis direction) and perpendicular or substantially perpendicular to the first point-of-view direction. The second point-of-view direction is perpendicular or substantially perpendicular to the direction of dentition 200 and the first point-of-view direction. The third point-of-view direction is perpendicular or substantially perpendicular to the direction of dentition 200 (in the example in FIG. 3, the Y-axis direction) and perpendicular or substantially perpendicular to the first point-of-view direction. The third point-of-view direction is perpendicular or substantially perpendicular to the direction of dentition 200 and the first point-of-view direction.

For dentition 200 including molar 375 in the mandible, the second point-of-view direction is a direction toward lingual side surface 382 and the third point-of-view direction is a direction toward buccal side surface 383. The third point-of-view direction is opposite to the second point-of-view direction.

Display 50 shows additional information representing first image 301, second image 302, and third image 303, in the vicinity of first image 301, second image 302, and third image 303. First additional information 351 for first image 301 is represented by characters "Main View." Second additional information 352 for second image 302 is represented by characters "View1." Third additional information 353 for third image 303 is represented by characters "View2."

A tooth that a user particularly desires to check is referred to as a "target tooth 360" below. In the present embodiment, information representing target tooth 360 (for example, identification information (identification number) of a tooth) can be input, for example, by an operation by the user onto a peripheral device (a keyboard 601 and a mouse 602 in FIG. 9 which will be described later) before scanning. Image processing apparatus 40 can identify target tooth 360 based on information representing target tooth 360. Any tooth may be designated as target tooth 360. For example, an abutment tooth is designated as target tooth 360. Display 50 shows target tooth information 310, and based thereon the user can identify target tooth 360. In the example in FIG. 3, target tooth information 310 is represented by a character "A". Target tooth 360 is a tooth on which the user focuses.

The user may designate target tooth 360 by performing the third operation. For example, the user directs an image pick-up surface of three-dimensional scanner 80 toward a tooth to be designated as a target tooth and performs the third operation. With such an operation, the user can designate target tooth 360.

Display 50 shows also a gingiva image which is an image not only of a tooth such as target tooth 360 but also of gingiva 365.

Display 50 shows a multi-image created by combination of a plurality of images (first image 301, second image 302, and third image 303) such that target tooth 360 in first image 301 is located substantially in a central portion of display area 50A. Display 50 shows first image 301, second image 302, and third image 303 in display area 50A such that any of an X coordinate position and a Y coordinate position in the display area is identical. In the example in FIG. 3, display 50 shows first image 301, second image 302, and third image 303 such that the Y coordinate is identical among first image 301, second image 302, and third image 303. The "Y coordinate being identical" means that Y coordinates of corresponding portions in first image 301, second image 302, and third image 303 are identical. For example, an arbitrary tooth may be set as the corresponding portion. For example, target tooth 360 is defined as the arbitrary tooth.

In the example in FIG. 3, under the control by image processing apparatus 40, display 50 shows first image 301, second image 302, and third image 303 such that the Y coordinates of target tooth 360 in first image 301, target tooth 360 in second image 302, and target tooth 360 in third image 303 are identical as shown with a chain dotted line L. In a modification, display 50 may show first image 301, second image 302, and third image 303 such that their "Y coordinates are substantially identical." Being substantially identical means that at least one of first image 301, second image 302, and third image 303 is displaced in Y coordinate from other images by a prescribed number of pixels. The prescribed number is preferably smaller and the prescribed number is set, for example, to "three".

Under the control by image processing apparatus 40, display 50 shows second image 302 at a position in a negative direction along the X axis of first image 301, with first image 301 being defined as the reference. Second image 302 is arranged with respect to first image 301, on a side of the lingual side surface of a tooth included in first image 301. Under the control by image processing apparatus 40, display 50 shows third image 303 at a position in a positive direction along the X axis of first image 301, with first image 301 being defined as the reference. Third image 303 is arranged with respect to first image 301, on a side of a buccal side surface included in first image 301.

Depending on a speed of movement of three-dimensional scanner 80 by a user, three-dimensional scanner 80 may not appropriately pick up an image of the inside of the oral cavity. For example, when a speed of movement of three-dimensional scanner 80 by the user is high, there may be a portion where image pick-up is not appropriately performed by three-dimensional scanner 80.

In the present embodiment, display 50 can show a portion where image pick-up has not appropriately been performed in various manners. For example, display 50 shows a multi-image in a manner in accordance with an amount of three-dimensional data acquired by three-dimensional scanner 80. In the example in FIG. 3, display 50 shows a supplemental image 312, an urging image 314, and a transparent region 316. In the example in FIG. 3, supplemental image 312 is an image hatched diagonally from top left to bottom right. In the example in FIG. 3, urging image 314 is an image hatched diagonally from bottom left to top right. Transparent region 316 is a region representing a portion where three-dimensional data is missing. In the example in FIG. 3, a color of transparent region 316 is identical to a color of the background of display area 50A.

Display 50 shows urging image 314 mainly at a portion superimposed on target tooth 360 (a tooth on which the user is focusing) and a portion in the vicinity of target tooth 360. Target tooth 360 is a tooth important for the user (the tooth on which the user is focusing). Urging image 314 is an image indicating that an amount of three-dimensional data is insufficient at the portion of target tooth 360 important for the user and at the portion in the vicinity of target tooth 360. Urging image 314 is an "image urging the user to scan again a portion where urging image 314 is shown," In other words, urging image 314 is an image that causes the user to recognize that low accuracy of three-dimensional data acquired by three-dimensional scanner 80 will be maintained unless the user scans again the portion where urging image 314 is shown. Urging image 314 is also an image that causes the user to recognize that design of a prosthesis which is a subsequent process will adversely be affected unless the user scans again the portion Where urging image 314 is shown.

Display 50 shows supplemental image 312 at a portion different from the portion superimposed on target tooth 360 and the portion in the vicinity of target tooth 360 (that is, a portion distant from target tooth 360). Supplemental image 312 is briefly defined as an image that causes the user to recognize that "three-dimensional data is insufficient in a portion where supplemental image 312 is shown and it is supplemented."

Transparent region 316 is a region indicating a portion Where three-dimensional data is missing. A color of transparent region 316 is identical to a color of the background of display area 50A. Transparent region 316 is a region that causes the user to recognize that "a large amount of three-dimensional data is insufficient as compared with supplemental image 312 and urging image 314.

FIG. 4 briefly shows correspondence between a manner of representation of an image on display 50 and a content of the manner of representation. FIG. 4 shows supplemental image 312 as a "supplemented portion." FIG. 4 shows urging image 314 as an "urging portion." FIG. 4 shows transparent region 316 as a "missing portion."

When target tooth 360 has not been identified, display 50 shows supplemental image 312 at a portion where three-dimensional data is slightly insufficient without showing urging image 314. Display 50 shows transparent region 316 at a portion where a large amount of three-dimensional data is insufficient.

FIG. 5 is a diagram showing an exemplary image shown on display 50 in the present embodiment. FIG. 5 (A) is a diagram showing an example in which display 50 shows the single point-of-view image shown in FIG. 2. FIG. 5 (B) is a diagram showing an example in which display 50 shows the multi-image shown in FIG. 3. In the present embodiment, the "single point-of-view image" is an image shown for allowing a user to rotate the image in display area 50A by operating a peripheral device (mouse 602 or the like) of image processing apparatus 40. In the present embodiment, in response to an operation by the user (the second operation onto scan button 802 which will be described later), display 50 can show any one of the single point-of-view image shown in FIG. 5 (A) and the multi-image shown in FIG. 5 (B). A representation mode in which the single point-of-view image is shown as in FIG. 5 (A) is referred to as a "single point-of-view representation mode." A representation mode in which the multi-image (first image 301, second image 302, and third image 303) is shown as in FIG. 5 (B) is referred to as a "multi-representation mode." The "multi-representation mode" is also referred to as a "multi-view mode." In the present embodiment, the "single point-of-view representation mode" is set as a default mode. A state that scanning by three-dimensional scanner 80 is being performed is referred to as "during scanning." A state that scanning by three-dimensional scanner 80 is not being performed is referred to as "during non-scanning."

For example, when the second operation (press-and-hold operation) is performed onto scan button 802 by the user while the "single point-of-view representation mode" has been set during scanning, display system 100 switches to the "multi-representation mode" shown in FIG. 5 (B). When the second operation (press-and-hold operation) is performed onto scan button 802 by the user while the "multi-representation mode" has been set during scanning, display system 100 switches to the "single point-of-view representation mode" shown in FIG. 5 (A). During non-scanning, as the user operates, for example, a peripheral device (a mouse or the like) of image processing apparatus 40, switching to any of the "single point-of-view representation mode" and the "multi-representation mode" can be made. During non-scanning, three-dimensional scanner 80 is not located in the oral cavity. Therefore, touch by the user to a peripheral device of image processing apparatus 40 may not give rise to a hygienic problem. In this case, the user may operate a peripheral device (a mouse or the like) of image processing apparatus 40.

The "single point-of-view representation mode" is a mode in which an image from a single point of view is shown and an image of the entire dentition is shown. For example, in the example in FIG. 5 (A), an image of right teeth from the buccal side surface and an image of left teeth from the lingual side surface are shown. The "multi-image mode" is a mode in which images from a plurality of points of view are shown and an image of dentition is locally shown. Thus, during scanning and during non-scanning, switching to any one of the "single point-of-view representation mode" and the "multi-representation mode" can be made in response to an operation by the user and hence convenience of the user can be improved.

[Use of Three-Dimensional Scanner]

Figure 6:
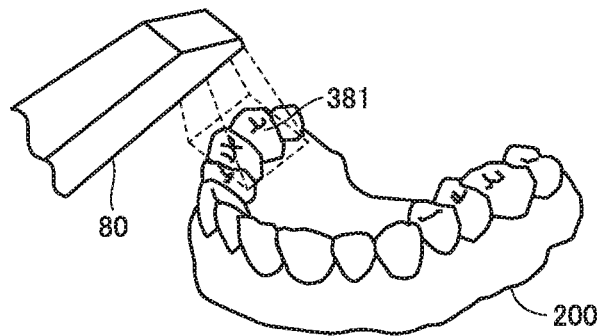
FIG. 6 is a diagram for illustrating use of a three-dimensional scanner.

FIG. 6 is a diagram for illustrating use of three-dimensional scanner 80. In the present embodiment, as shown in FIG. 6, a manufacturer of three-dimensional scanner 80 recommends the user to set a position from which scanning by three-dimensional scanner 80 is to be started to occlusal surface 381 of rearmost molar 375. For example, an operation manual of three-dimensional scanner 80 recommends that the position from which scanning by three-dimensional scanner 80 is to be started be set to occlusal surface 381 of rearmost molar 375. Alternatively, for example, at prescribed timing before the user starts scanning, display system 100 may carry out urging control for urging the user to set the position from which scanning is to be started to occlusal surface 381 of rearmost molar 375. Urging control refers, for example, to control for having display 50 show an image of characters "set a position from which scanning is to be started to the occlusal surface of the rearmost molar." Urging control may be, for example, control for having image processing apparatus 40 output voice "set a position from which scanning is to be started to occlusal surface 381 of rearmost molar 375."

The present embodiment assumes that occlusal surface 381 of molar 375 is a portion of which image is picked up first (initially) by three-dimensional scanner 80.

Figure 7:
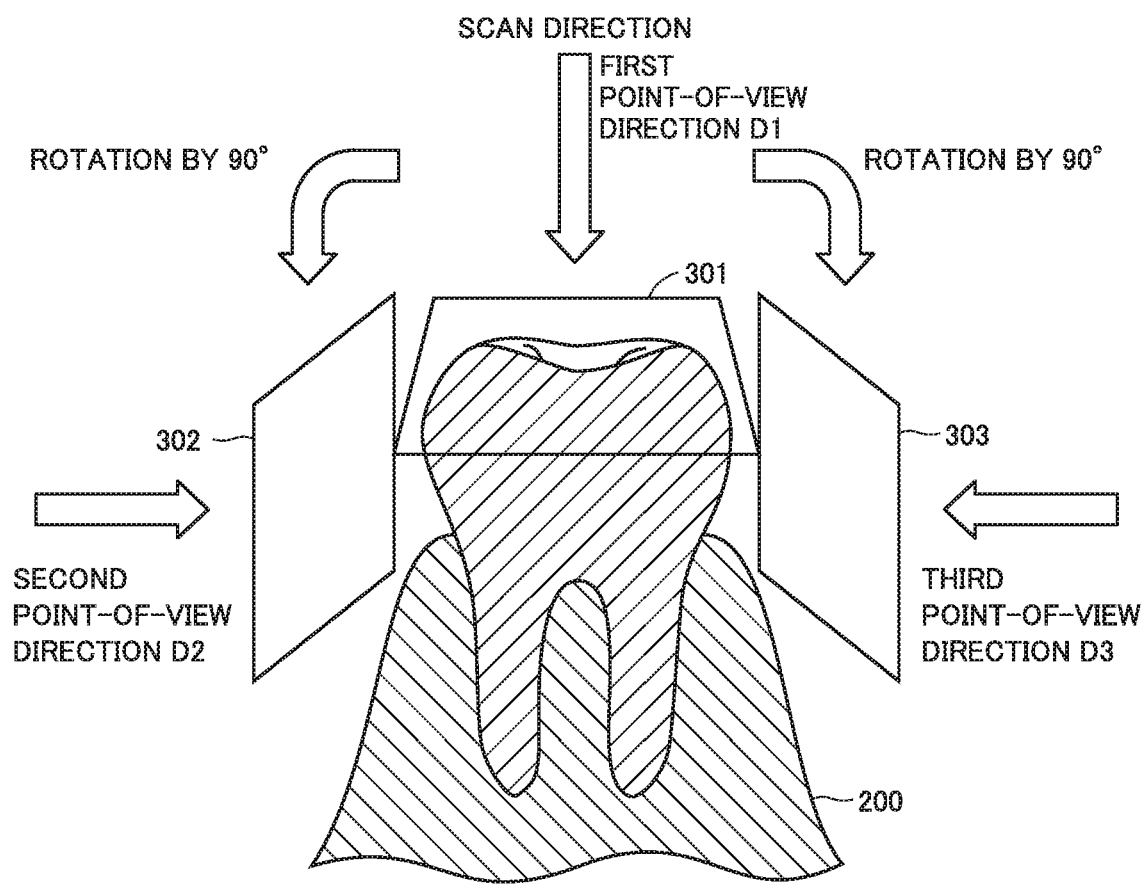
FIG. 7 is a diagram showing a concept of scanning by the three-dimensional scanner and a multi-image.
Figure 8:
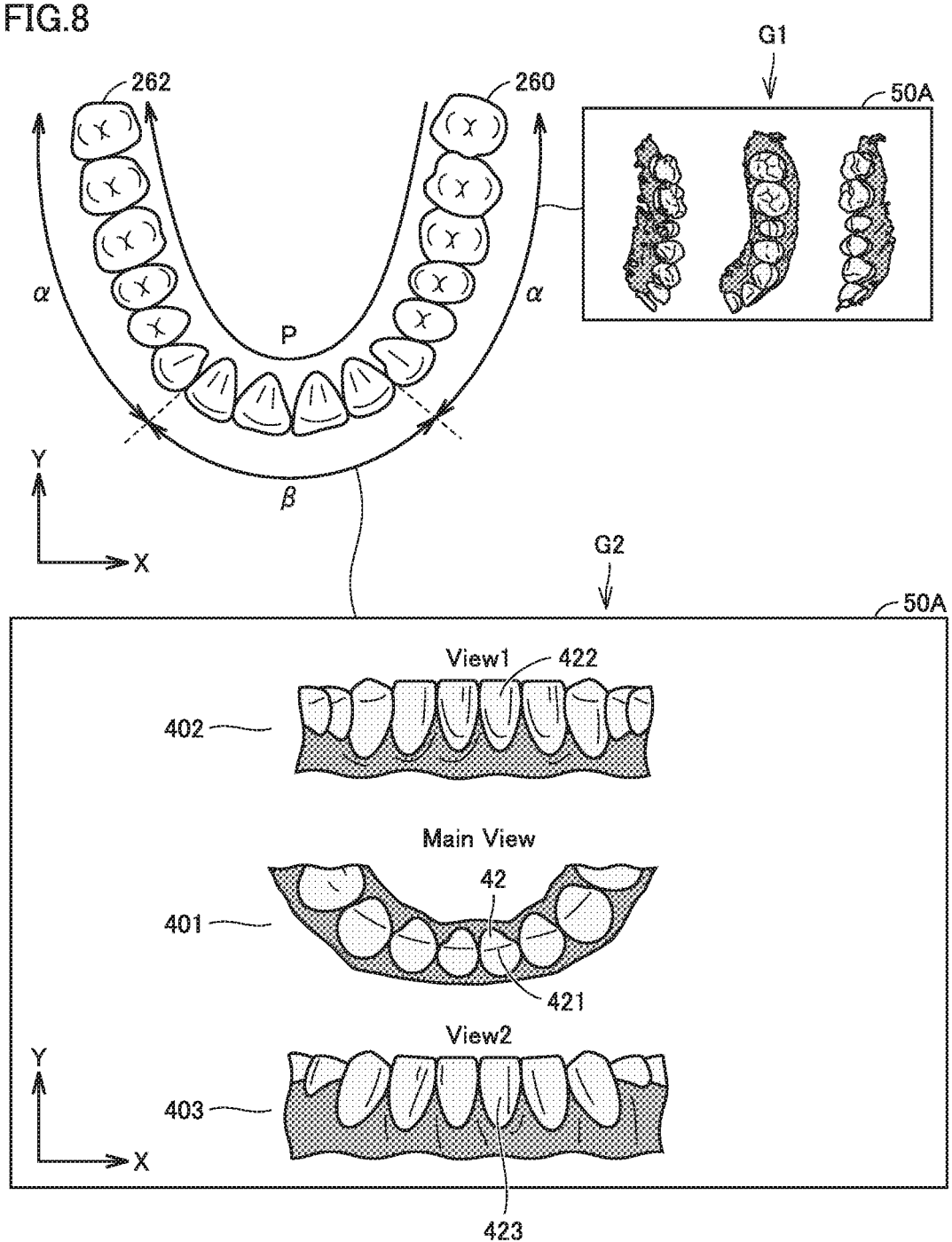
FIG. 8 is a diagram for illustrating image pick-up of the entire dentition (dental arch) in mandible.

FIG. 7 is a diagram showing relation between scanning by three-dimensional scanner 80 and a multi-image. As shown in FIG. 7, for example, when a direction of scanning by three-dimensional scanner 80 is first point-of-view direction D1 toward dentition 200, display 50 shows first image 301 in first point-of-view direction D1 (viewed in first point-of-view direction D1), second image 302 in second point-of-view direction D2 (viewed in second point-of-view direction D2), and third image 303 in third point-of-view direction D3 (viewed in third point-of-view direction D3), FIG. 8 is a diagram for illustrating image pick-up of the entire dentition 200 (dental arch) in the mandible by a user with the use of three-dimensional scanner 80. In the example in FIG. 8, an image is picked up along a direction of dentition of the dental arch as shown with an arrow P. A right rearmost molar 260 is a tooth from which scanning is started and a left rearmost molar 262 is a tooth at which scanning ends.

Display 50 shows a multi-image at a representation position in accordance with a direction of movement of three-dimensional scanner 80 as a relative representation position of first image 301, second image 302, and third image 303, based on multi-image data which will be described later from image processing apparatus 40. Image processing apparatus 40 can identify a direction of movement of three-dimensional scanner 80 based on a motion signal (see FIG. 10) from motion sensor 804 contained in three-dimensional scanner 80.

For example, when three-dimensional scanner 80 picks up an image of dentition 200 along a direction of dentition (dentition within a range α) which is substantially the same as the Y-axis direction, as shown in an image G1 in FIG. 8 (a picture the same as in FIG. 3), first image 301 is shown in the center of display area 50A, second image 302 is shown at a position in the negative direction along the X axis in first image 301, and third image 303 is shown at a position in the positive direction along the X axis in first image 301. When image pick-up by three-dimensional scanner 80 is performed along the direction of dentition (dentition within range α) which is substantially the same as the Y-axis direction, display 50 shows first image 301 and shows second image 302 and third image 303 on opposing sides of first image 301 along the X-axis direction.

When three-dimensional seamier 80 picks up an image of dentition 200 along a direction of dentition (dentition within a range β) which is substantially the same as the X-axis direction, display 50 shows an image G2. Image G2 will now be described.

As shown in image G2, when three-dimensional scanner 80 picks up an image of dentition 200 along the direction of dentition (dentition within range β) which is substantially the same as the X-axis direction, display 50 shows a plurality of images different in point of view toward dentition 200 (in the example in FIG. 8, a first image 401, a second image 402, and a third image 403).

First image 401 is an image showing dentition 200 in the first point-of-view direction (dentition 200 viewed in the first point-of-view direction). Second image 402 is an image showing dentition 200 in the second point-of-view direction (dentition 200 viewed in the second point-of-view direction). Third image 403 is an image showing dentition 200 in the third point-of-view direction (dentition 200 viewed in the third point-of-view direction).

The first point-of-view direction (the point-of-view direction in first image 401) is a direction from a point of view toward an incisal edge 421 of an incisor 42 (a tooth within range β). The second point-of-view direction (the point-of-view direction in second image 402) is a direction from a point of view toward a lingual side surface 422. The third point-of-view direction (the point-of-view direction in third image 403) is a direction from a point of view toward a labial side surface 423.

In other words, the first point-of-view direction is a direction of height of incisor 42 (the Z-axis direction). The second point-of-view direction is perpendicular or substantially perpendicular to the direction of dentition 200 (in the example in FIG. 8, the X-axis direction) and perpendicular or substantially perpendicular to the first point-of-view direction. The second point-of-view direction is perpendicular or substantially perpendicular to the direction of dentition 200 and the first point-of-view direction. The third point-of-view direction is perpendicular or substantially perpendicular to the direction of dentition 200 (in the example in FIG. 3, the X-axis direction) and perpendicular or substantially perpendicular to the first point-of-view direction. The third point-of-view direction is perpendicular or substantially perpendicular to the direction of dentition 200 and the first point-of-view direction.

Regarding dentition 200 including incisor 42 in the mandible, the second point-of-view direction is a direction toward lingual side surface 422 and the third point-of-view direction is a direction toward labial side surface 423. The third point-of-view direction is opposite to the second point-of-view direction.

In the example in image G2 in FIG. 8, display 50 shows first image 401, second image 402, and third image 403 such that an X coordinate is identical among first image 401, second image 402, and third image 403. The "X coordinate being identical" means that X coordinates of corresponding portions in first image 401, second image 402, and third image 403 are identical.

In a modification, display 50 may show first image 401, second image 402, and third image 403 such that their "X coordinates are substantially identical."

Display 50 shows second image 402 at a position in the positive direction along the Y axis in first image 401, with first image 401 being defined as the reference. Display 50 shows third image 403 at a position in the negative direction along the Y axis in first image 401, with first image 401 being defined as the reference.

In the present embodiment, a canine tooth is assumed to be included in dentition within range α. When image pickup of a canine tooth is performed by three-dimensional scanner 80, display 50 shows first image 301, second image 302, and third image 303 in the manner in FIG. 3.

When an image shown on display 50 includes molar 375 and the canine tooth on the right in the mandible, first image 301 is an image from a point of view toward occlusal surface 381. Second image 302 is an image from a point of view toward a side surface (for example, lingual side surface 382). Third image 303 is an image from a point of view toward a side surface (for example, buccal side surface 383).

When an image shown on display 50 includes incisor 42 in the mandible, first image 401 is an image from a point of view toward incisal edge 421. Second image 402 is an image from a point of view toward a side surface (for example, lingual side surface 422). Third image 403 is an image from a point of view toward a side surface (for example, labial side surface 423).

Though not particularly shown, when an image shown on display 50 includes a molar and a canine tooth on the left in the mandible, the first image is an image from a point of view toward the occlusal surface of the molar and the canine tooth. The second image is an image from a point of view toward a side surface (for example, the buccal side surface) of the molar and the canine tooth. The third image is an image from a point of view toward a side surface (for example, the lingual side surface) of the molar and the canine tooth.

When an image shown on display 50 includes a molar and a canine tooth on the right in the maxilla, the first image is an image from a point of view toward the occlusal surface of the molar and the canine tooth. The second image is an image from a point of view toward a side surface (for example, a palatal side surface) of the molar and the canine tooth. The third image is an image from a point of view toward a side surface (for example, the buccal side surface) of the molar and the canine tooth.

When an image shown on display 50 includes a molar and a canine tooth on the left in the maxilla, the first image is an image from a point of view toward the occlusal surface of the molar and the canine tooth. The second image is an image from a point of view toward a side surface (for example, the buccal side surface) of the molar and the canine tooth. The third image is an image from a point of view toward a side surface (for example, the palatal side surface) of the molar and the canine tooth.

When an image shown on display 50 includes an incisor in the maxilla, the first image is an image from a point of view toward the incisal edge of the incisor. The second image is an image from a point of view toward a side surface (for example, the palatal side surface) of the incisor. The third image is an image from a point of view toward a side surface (for example, the labial side surface) of the incisor.

[Hardware Configuration of Image Processing Apparatus]

Figure 9:
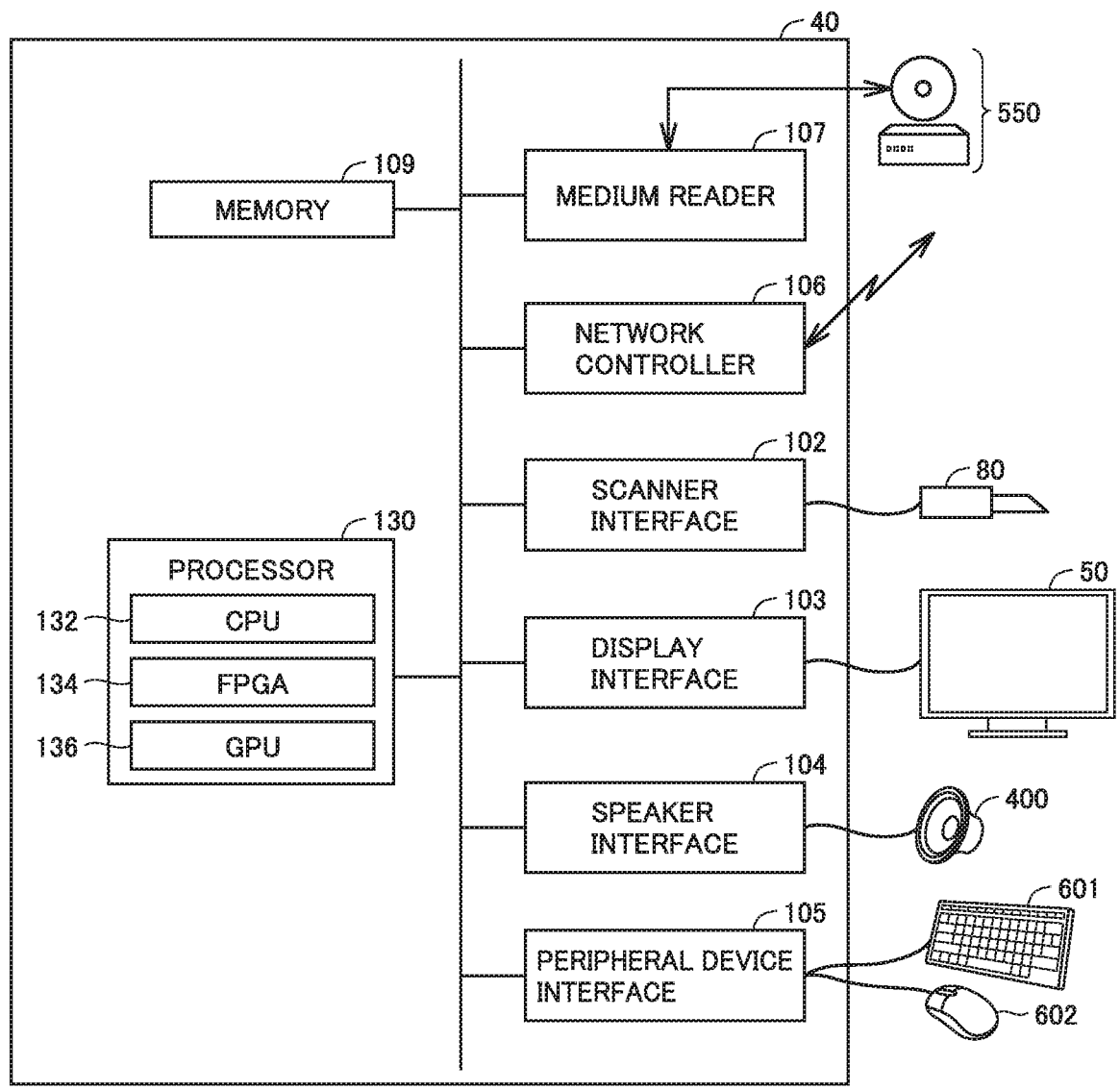
FIG. 9 is a diagram showing an exemplary hardware configuration of an image processing apparatus.

FIG. 9 is a diagram showing an exemplary hardware configuration of image processing apparatus 40. As shown in FIG. 9, image processing apparatus 40 includes as main hardware elements, a scanner interface 102, a display interface 103, a speaker interface 104, a peripheral device interface 105, a network controller 106, a medium reader 107, a memory 109, and a processor 130.

Scanner interface 102 is an interface for connection of three-dimensional scanner 80 and serves for input and output of data between image processing apparatus 40 and three-dimensional scanner 80.

Display interface 103 is an interface for connection of display 50 and serves for input and output of data between image processing apparatus 40 and display 50. Speaker interface 104 is an interface for connection of a speaker 400 and serves for input and output of data between image processing apparatus 40 and speaker 400.

Peripheral device interface 105 is an interface for connection of peripheral devices such as keyboard 601 and mouse 602 and serves for input and output of data between image processing apparatus 40 and the peripheral devices.

Network controller 106 transmits and receives data to and from an external apparatus (not shown) through a network. Network controller 106 is in conformity with any communication scheme such as Ethernet™, wireless local area network (LAN), or Bluetooth®.

Medium reader 107 reads various types of data such as scanning information stored in a removable disc 550.

Memory 109 provides a storage area for temporary storage of a program code or a work memory in execution of an arbitrary program by processor 130. Memory 109 includes a volatile memory device such as a dynamic random access memory (DRAM) or a static random access memory (SRAM). Memory 109 includes a non-volatile memory device such as a read only memory (ROM).

Processor 130 is an operation entity that performs various types of processing of image processing apparatus 40 by executing various programs and represents an exemplary computer. Processor 130 is implemented, for example, by a central processing unit (CPU) 132, a field-programmable gate array (FPGA) 134, and a graphics processing unit (GPU) 136. CPU 132 performs various types of processing (image data generation processing) based on a program stored in memory 109. A processor without including FPGA 134 may be applicable. A computer readable storage medium that stores various programs executed by processor 130 may be distributed as a program product. The storage medium stores a program in a non-transitory manner.

[Exemplary Functional Configuration of Image Processing Apparatus 40]

Figure 10:
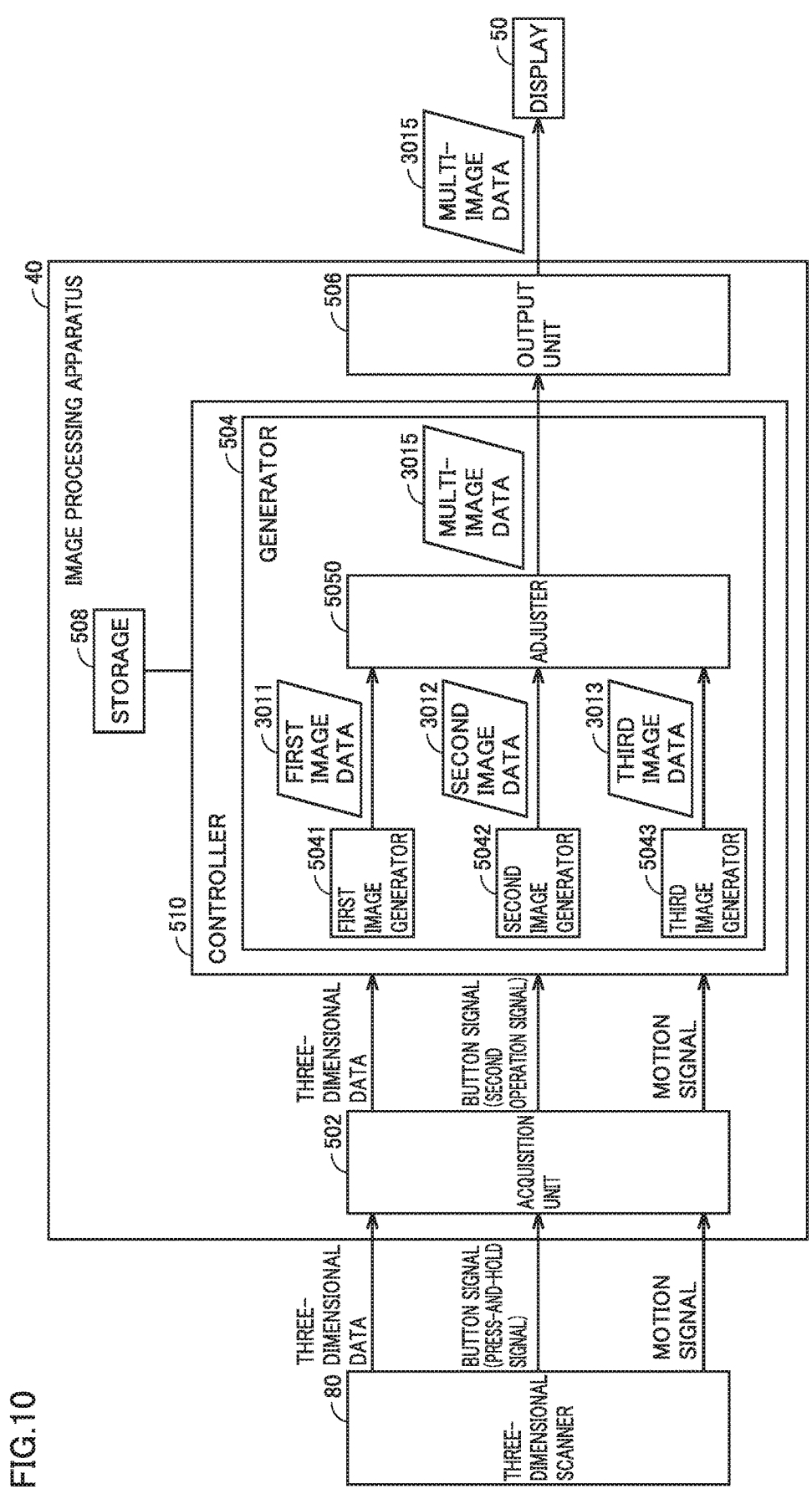
FIG. 10 is a diagram showing an exemplary functional configuration of the image processing apparatus.

FIG. 10 is a diagram showing an exemplary functional configuration of image processing apparatus 40. Image processing apparatus 40 includes an acquisition unit 502, an output unit 506, a storage 508, and a controller 510. Acquisition unit 502 corresponds to scanner interface 102. Output unit 506 corresponds to display interface 103. Storage 508 corresponds to memory 109. Acquisition unit 502 and output unit 506 may be interpreted as functions of controller 510. Storage 508 stores image data and various flags. The flag includes, for example, a flag indicating a "single point-of-view representation mode" and a flag indicating a "multi-representation mode." The flag that indicates control in the "single point-of-view representation mode" is referred to as a "single point-of-view representation flag" below. The flag that indicates control in the "multi-representation mode" is referred to as a "multi-representation flag." Controller 510 corresponds to processor 130.

Controller 510 has a function of a generator 504. Generator 504 further includes functions of a first image generator 5041, a second image generator 5042, a third image generator 5043, and an adjuster 5050. Though first image generator 5041, second image generator 5042, and third image generator 5043 are individually shown in FIG. 10 for the sake of convenience, generator 504 may perform processing by first image generator 5041, second image generator 5042, and third image generator 5043.

Three-dimensional scanner 80 transmits three-dimensional data obtained by image pick-up of dentition in the oral cavity to image processing apparatus 40, As described previously, three-dimensional scanner 80 picks up an image each time extremely short time period T elapses. Therefore, three-dimensional data is transmitted from three-dimensional scanner 80 to image processing apparatus 40 each time extremely short time period T elapses.

When scan button 802 (see FIG. 1) arranged in three-dimensional scanner 80 is operated, three-dimensional scanner 80 transmits a button signal indicating the operation to image processing apparatus 40. For example, when the user performs the second operation onto scan button 802, three-dimensional scanner 80 transmits a second operation signal as the button signal to image processing apparatus 40. The second operation signal corresponds to a "prescribed signal" in the present disclosure.

Three-dimensional scanner 80 transmits a motion signal indicating an operation by a user detected by motion sensor 804 (see FIG. 1) contained in three-dimensional scanner 80 to image processing apparatus 40. The motion signal is a signal, for example, indicating a direction of movement of three-dimensional scanner 80. Image processing apparatus 40 can recognize, for example, switching of a direction of movement of three-dimensional scanner 80 based on the motion signal. For example, as described with reference to FIG. 8, when the user moves three-dimensional scanner 80 along a direction of dentition in the dental arch (arrow P), image processing apparatus 40 can recognize based on the motion signal that the direction of movement of three-dimensional scanner 80 has been switched from the Y-axis direction to the X-axis direction.

Acquisition unit 502 acquires three-dimensional data, a button signal (second operation signal), and a motion signal from three-dimensional scanner 80.

Generator 504 generates single point-of-view image data and multi-image data 3015 which will be described later based on three-dimensional data from three-dimensional scanner 80. Single point-of-view image data and multi-image data 3015 will also collectively be referred to as "image data" below.

An approach to generation of single point-of-view image data by generator 504 will initially be described. Generator 504 generates single point-of-view image data based on three-dimensional data acquired by acquisition unit 502. Single point-of-view image data is data for display 50 to show a single point-of-view image shown in FIG. 5 (A). Generator 504 generates single point-of-view image data by converting three-dimensional data acquired by acquisition unit 502 into a format for representation (which is referred to as a "representation format" below). Each time generator 504 receives three-dimensional data, it converts the three-dimensional data into single point-of-view image data and has storage 508 store (accumulate) the converted single point-of-view image data. Controller 510 incrementally updates single point-of-view image data in storage 508 based on such accumulation.

An approach to generation of multi-image data by generator 504 will now be described. Generator 504 generates also multi-image data based on three-dimensional data acquired by acquisition unit 502. Generator 504 generates multi-image data based on three-dimensional data before conversion into a format for representation. Generator 504 may convert generated multi-image data into the format for representation. Generator 504 does not have to convert generated multi-image data into the format for representation. Generator 504 may generate multi-image data based on three-dimensional data converted into the format for representation.

Image processing apparatus 40 converts three-dimensional data into a prescribed format required for design of a prosthesis and has storage 508 store the three-dimensional data. Examples of the prescribed format include a standard triangulated language (STL) format. In order to design a prosthesis of high quality, three-dimensional data of three-dimensional positions appropriate in density and high in accuracy is required. Therefore, as described previously, by showing urging image 314, the user is urged to scan again a portion where an amount of data does not satisfy data requirement.

Multi-image data is data for display 50 to show a multi-image shown in FIG. 3. Multi-image data includes first image data 3011, second image data 3012, and third image data 3013. First image data 3011 is image data of first image 301. Second image data 3012 is image data of second image 302. Third image data 3013 is image data of third image 303.

In the present embodiment, generator 504 generates multi-image data of all dentitions in the oral cavity of which images were picked up by three-dimensional scanner 80. Therefore, under the control by image processing apparatus 40, display 50 can show a multi-images of all dentitions (an image from a plurality of points of view). Therefore, a user can check an image of all dentitions from a plurality of points of view.

In a modification, generator 504 may generate multi-image data of dentition only within a predetermined range from target tooth 360 inclusive of target tooth 360. For example, a range shown in FIG. 3 is defined as the predetermined range. In the modification, generator 504 does not generate multi-image data of dentition out of the predetermined range. For example, generator 504 generates multi-image data based on the multi-image shown in FIG. 3 whereas it does not generate multi-image data of dentition other than dentition shown in FIG. 3 (dentition out of the predetermined range). For example, when a target tooth is included in teeth in the mandible as shown in FIG. 3, generator 504 generates multi-image data of dentition including the target tooth shown in FIG. 3 but does not generate multi-image data of dentition in the mandible out of the range shown in FIG. 3 and multi-image data of dentition in the maxilla. In such a modification, loads imposed by processing for generating multi-image data could be lower than in an image processing apparatus that generates multi-image data of all dentitions.

In the present embodiment, first image generator 5041 generates first image data 3011 of first image 301 (see FIG. 3). Second image generator 5042 generates second image data 3012 of second image 302. Third image generator 5043 generates third image data 3013 of third image 303. In the present embodiment, first image data 3011, second image data 3012, and third image data 3013 are each two-dimensional image data. Two-dimensional image data includes, for example, information on a two-dimensional coordinate (an X coordinate and a Y coordinate) and color information (for example, RGB) associated with the information on the coordinate.

An approach to generation of first image data 3011, second image data 3012, and third image data 3013 by generator 504 will be described. In the present embodiment, first image generator 5041 generates first image data 3011 of first image 301 showing dentition 200 in first point-of-view direction D1. As described with reference also to FIG. 6, a manufacturer of three-dimensional seamier 80 recommends a user to set a position from which scanning by three-dimensional scanner 80 is to be started to occlusal surface 381 of rearmost molar 375. Therefore, first image generator 5041 generates as first image data 3011, image data of an image that is picked up first (an image of occlusal surface 381) at the time when scanning processing is started (when the second operation is performed onto scan button 802). For example, first image generator 5041 extracts first image data 3011 from three-dimensional data transmitted from acquisition unit 502.

Second image generator 5042 generates second image data 3012 by extracting second image data 3012 of second image 302 showing dentition 200 in second point-of-view direction D2 from three-dimensional data transmitted from acquisition unit 502. For example, second image generator 5042 generates second image data 3012 by multiplying three-dimensional data transmitted from acquisition unit 502 by a rotation matrix for rotation by an angle corresponding to second point-of-view direction D2 (for example, 90 degrees shown in FIG. 7).

Third image generator 5043 generates third image data 3013 by extracting third image data 3013 of third image 303 showing dentition 200 in third point-of-view direction D3 from three-dimensional data transmitted from acquisition unit 502. For example, third image generator 5043 generates third image data 3013 by multiplying three-dimensional data transmitted from acquisition unit 502 by a rotation matrix for rotation by an angle corresponding to third point-of-view direction D3 (for example, 90 degrees shown in FIG. 7).

First image generator 5041, second image generator 5042, and third image generator 5043 may generate through another type of calculation, first image data 3011, second image data 3012, and third image data 3013, respectively. For example, first image generator 5041 may extract as first image data 3011, three-dimensional data corresponding to the occlusal surface, of three-dimensional data transmitted from acquisition unit 502. Second image generator 5042 may extract as second image data 3012, three-dimensional data of a portion at an angle corresponding to second point-of-view direction D2 (for example, 90 degrees shown in FIG. 7) from three-dimensional data extracted as first image data 3011, of the three-dimensional data transmitted from acquisition unit 502. Third image generator 5043 may extract as third image data 3013, three-dimensional data of a portion at an angle corresponding to third point-of-view direction D3 (for example, 90 degrees shown in FIG. 7) from three-dimensional data extracted as first image data 3011, of the three-dimensional data transmitted from acquisition unit 502.

A manufacturer of three-dimensional scanner 80 recommends a user to set a position from which scanning by three-dimensional scanner 80 is to be started to occlusal surface 381 of rearmost molar 375. Therefore, it is dentition including molar 375 that is initially subjected to image pick-up by three-dimensional scanner 80, and a direction of a point of view toward occlusal surface 381 of this dentition is defined as first point-of-view direction D1. Image processing apparatus 40 generates second image data 3012 of an image including a side surface of dentition, with a direction resulting from conversion of first point-of-view direction D1 by an angle θ in the X-axis direction being defined as second point-of-view direction D2. A prescribed angle θ in the present embodiment is set to 90 degrees. Angle θ may be smaller than 90 degrees and may be set, for example, to 30 degrees or 45 degrees. Image processing apparatus 40 generates third image data 3013 of an image including a side surface of dentition, with a direction resulting from conversion of first point-of-view direction D1 by an angle −θ in the X-axis direction being defined as third point-of-view direction D3.

The occlusal surface is shown in a part of second image 302 and third image 303 with directions toward side surfaces of dentition being defined as points of view, based on second image data 3012 and third image data 3013. First image 301 mainly focusing on occlusal surface 381 is shown, and second image 302 and third image 303 including a part of occlusal surface 381 while mainly focusing on side surfaces of dentition are shown. Consequently, a user readily recognizes relation among first image 301, second image 302, and third image 303 based on common occlusal surface 381.

Adjuster 5050 adjusts first image data 3011, second image data 3012, and third image data 3013 such that positional relation in representation of first image 301, second image 302, and third image 303 in showing first image 301, second image 302, and third image 303 on display 50 corresponds. For example, generator 504 has generated first image data 3011, second image data 3012, and third image data 3013 once stored in a prescribed work area (for example, an area in storage 508) and adjusts first image data 3011, second image data 3012, and third image data 3013 in that work area.

As described previously, the position from which scanning by three-dimensional scanner 80 is to be started is set to occlusal surface 381 of molar 375. Therefore, based on the disclosure in FIG. 8, a direction of movement of three-dimensional scanner 80 is set to the Y-axis direction. When generator 504 determines that the direction of movement of three-dimensional scanner 80 has been set to the Y-axis direction based on a motion signal, generator 504 adjusts first image data 3011, second image data 3012, and third image data 3013 such that a picture as shown in FIG. 3 is shown.

For example, adjuster 5050 adjusts first image data 3011, second image data 3012, and third image data 3013 such that the Y coordinate in display area 50A of first image 301, second image 302, and third image 303 is identical.

When adjuster 5050 determines that the direction of movement of three-dimensional scanner 80 has been set to the X-axis direction based on the motion signal, generator 504 adjusts first image data 3011, second image data 3012, and third image data 3013 such that the picture as shown in image G2 in FIG. 8 is shown.

For example, adjuster 5050 adjusts first image data 3011, second image data 3012, and third image data 3013 such that the X coordinate in display area 50A of first image 401, second image 402, and third image 403 is identical.

Adjustment by adjuster 5050 is made by changing information on the coordinate (the X coordinate and the Y coordinate) and color information of first image data 3011, second image data 3012, and third image data 3013.

In the present embodiment, a generation step of generating first image data 3011, second image data 3012, and third image data 3013 and an adjustment step of adjusting first image data. 3011, second image data 3012, and third image data. 3013 performed by generator 504 are described as being separate from each other. Generator 504, however, may perform the generation step and the adjustment step in an integrated manner. For example, generator 504 may generate first image data 3011, second image data 3012, and third image data 3013 such that first image 301 showing dentition 200 in first point-of-view direction D1, second image 302 showing dentition 200 in second point-of-view direction D2 different from first point-of-view direction D1, and third image 303 showing dentition 200 in third point-of-view direction D3 different from first point-of-view direction D1 and second point-of-view direction D2 are shown on display 50 in corresponding positional relation.

Adjuster 5050 outputs adjusted first image data 3011, second image data 3012, and third image data 3013 as multi-image data 3015. Adjuster 5050 has storage 508 store multi-image data 3015.

Output unit 506 outputs multi-image data 3015 to display 50. Display 50 shows an image based on the image data.

In the present embodiment, under the control in the single point-of-view representation mode (when the second operation onto scan button 802 is not performed), output unit 506 outputs single point-of-view image data to display 50. Under the control in the multi-representation mode (when the second operation onto scan button 802 is performed), output unit 506 outputs multi-image data 3015 to display 50.

In the present embodiment, in the single point-of-view representation mode, a single point-of-view image shown on display 50 and a single point-of-view image based on single point-of-view image data stored in storage 508 are identical to (synchronous with) each other. In the present embodiment, in the multi-representation mode, a multi-image shown on display 50 and a multi-image based on multi-image data 3015 stored in storage 508 are identical to (synchronous with) each other. In a modification, in the multi-representation mode, storage 508 may store first image data 3011, second image data 3012, and third image data 3013 of all dentitions 200 of which images were picked up, whereas display 50 may show first image 301, second image 302, and third image 303 of target tooth 360.

Display 50 shows an image based on image data output from output unit 506. For example, when output unit 506 outputs single point-of-view image data, display 50 shows a single point-of-view image (see FIG. 2). When output unit 506 outputs multi-image data 3015, display 50 shows a multi-image (image G1 or image G2 in FIG. 8).

Supplemental image 312, urging image 314, and transparent region 316 described with reference to FIG. 4 will now be described from a point of view of generation of image data by generator 504. As shown also in FIG. 4, supplemental image 312 shows a supplemented portion, urging image 314 shows an urging portion, and transparent region 316 shows a missing portion.

In the present embodiment, generator 504 generates image data in accordance with an amount of three-dimensional data acquired by acquisition unit 502. In the present embodiment, a prescribed region R is predetermined.

Prescribed region R will be described below. Prescribed region R refers, for example, to a partial region of display area 50A. Prescribed region R refers, for example, to a region in display area 50A where a dentition image is shown based on three-dimensional data acquired by three-dimensional scanner 80 in image pick-up once. Prescribed region R refers, for example, to one region obtained by equally dividing display area 50A into N (N being an integer equal to or larger than two) parts. An amount of three-dimensional data allowing representation of an image with all pixels in prescribed region R is denoted as D max. Another region may be defined as prescribed region R.

An amount of three-dimensional data acquired by acquisition unit 502 being D max in prescribed region R means that acquisition unit 502 has acquired 100% of three-dimensional data. An amount of three-dimensional data in prescribed region R being smaller than D max means that an amount of three-dimensional data in prescribed region R is insufficient. In the present embodiment, a first threshold value Th1 and a second threshold value Th2 are determined for an amount of three-dimensional data.

D max is defined as first threshold value Th1. A value calculated by multiplying D max by a prescribed coefficient is defined as second threshold value Th2, and for example, "0.7×D max" is defined as second threshold value Th2. First threshold value Th1 corresponds to the "threshold value" in the present disclosure. In a modification, a value calculated by multiplying D max by a coefficient close to one (for example, 0.99) may be adopted as first threshold value Th1.

When generator 504 determines that an amount D of three-dimensional data in prescribed region R is D max, the three-dimensional data is sufficient in prescribed region R and no image is added.

When generator 504 determines that amount D of three-dimensional data in prescribed region R is smaller than D max and equal to or larger than second threshold value Th2 (that is, D max>D≥Th (=0.7× D max)), three-dimensional data is slightly missing in prescribed region R. Generator 504 identifies a missing portion (which is referred to as a "first missing portion" below) in prescribed region R. The generator generates supplemental image data for supplemental image 312 (see FIG. 3). Generator 504 provides the first missing portion with supplemental image data. Urging image data corresponds to "first additional data" in the present disclosure.

When a user has designated target tooth 360, generator 504 determines whether or not the first missing portion is in the vicinity of target tooth 360. For example, when the generator determines that the number of pixels between the first missing portion and a portion of target tooth 360 is equal to or larger than a predetermined threshold value E, generator 504 determines that the first missing portion is not in the vicinity of target tooth 360. When generator 504 determines that the number of pixels between the first missing portion and the portion of target tooth 360 is smaller than threshold value E, it determines that the first missing portion is in the vicinity of target tooth 360. When generator 504 determines that the first missing portion is in the vicinity of target tooth 360, it generates urging image data for urging image 314. Generator 504 provides the first missing portion with urging image data. Urging image data corresponds to the "second additional data" in the present disclosure. When generator 504 determines that the first missing portion is not in the vicinity of target tooth 360, it generates supplemental image data for supplemental image 312. Generator 504 provides the first missing portion with supplemental image data.

When amount D of three-dimensional data in prescribed region R is determined as D<second threshold value Th2 (=0.7×D max), a large amount of three-dimensional data is missing in prescribed region R. Generator 504 provides a missing portion (which is referred to as a "second missing portion" below) in prescribed region R with no image data.

Amount D of three-dimensional data in prescribed region. R being equal to or larger than second threshold value Th2 in the present embodiment means that "three-dimensional data is sufficient." Amount D of three-dimensional data in prescribed region R being smaller than second threshold value Th2 means that "three-dimensional data is insufficient." Generator 504 generates image data of only a portion where three-dimensional data is sufficient.

Generator 504 can thus have supplemental image 312 shown on display 50 as shown in FIG. 3, by providing the first missing portion with supplemental image data. Generator 504 can have urging image 314 shown on display 50 as shown in FIG. 3, by providing the first missing portion with urging image data. Generator 504 can have transparent region 316 shown on display 50 as shown in FIG. 3, by generating image data of only a portion where three-dimensional data is sufficient.

At least one of first threshold value Th1 and second threshold value Th2 may be different between determination as to whether or not to generate supplemental image 312 and determination as to whether or not to generate urging image 314. For determination of an amount of three-dimensional data by generator 504, another approach may be employed without being limited to the approach above.

[Flowchart of Display System]

Figure 11:
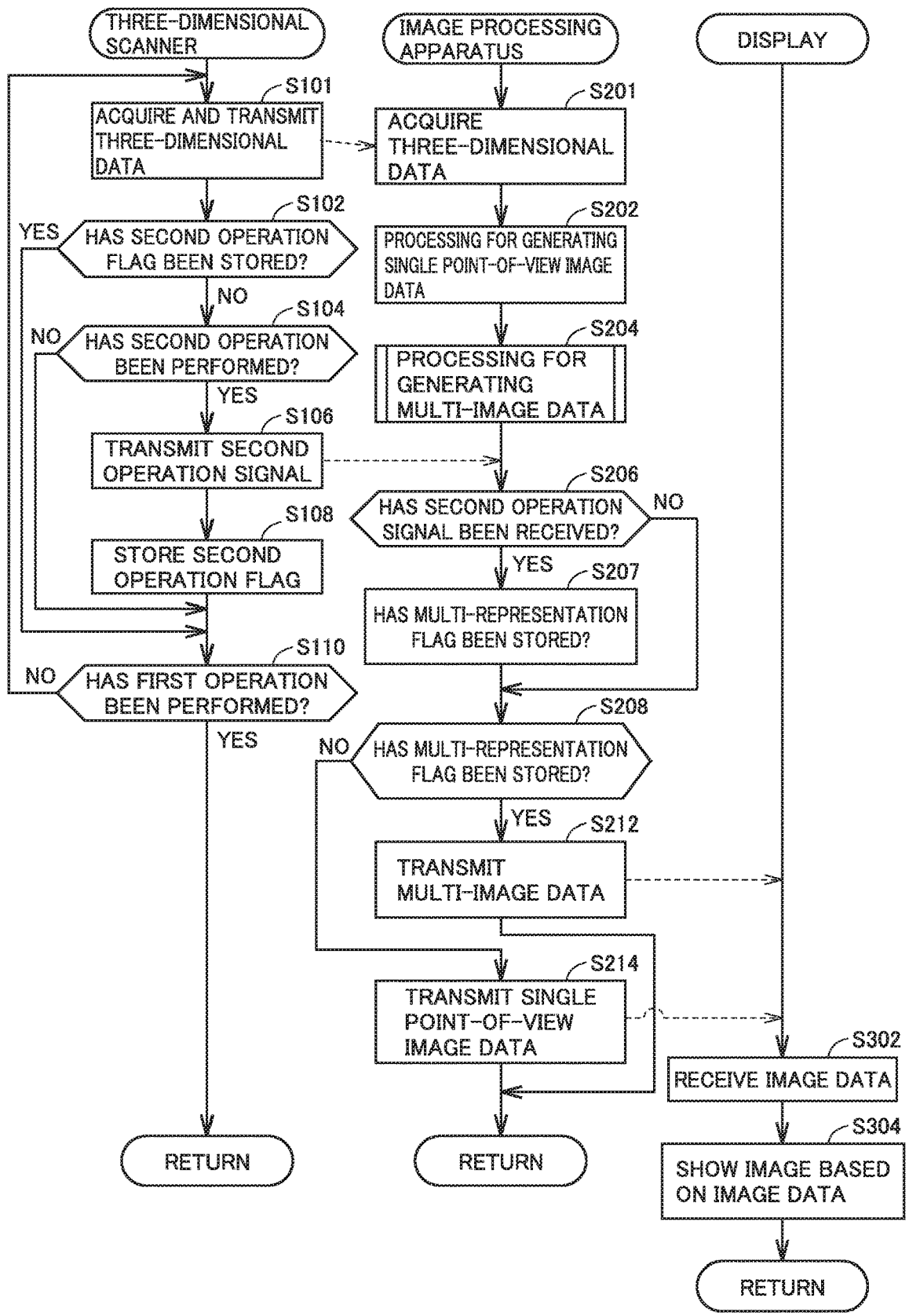
FIG. 11 is a diagram for illustrating a flowchart of the display system during scanning.

FIG. 11 is a diagram for illustrating a flowchart of display system 100 during scanning by three-dimensional scanner 80. Processing in display system 100 during scanning by three-dimensional scanner 80 will be described with reference to FIG. 11. Processing during scanning shown in the flowchart in FIG. 11 is started when a prescribed condition is satisfied. The prescribed condition is, for example, a condition that power of each of three-dimensional scanner 80 and image processing apparatus 40 is on, an application for scanning has been launched in image processing apparatus 40, and the first operation onto scan button 802 of three-dimensional scanner 80 is performed to start the scan mode. Display 50 shows an image based on image data from image processing apparatus 40 at the timing of reception of that image data while power of display 50 is on.

In step S101, three-dimensional scanner 80 acquires three-dimensional data by image pick-up of dentition 200 in the oral cavity and transmits the three-dimensional data to image processing apparatus 40. Except for a prescribed case (for example, when the first operation onto scan button 802 is performed again or when power is turned off), processing from step S101 to step S110 shown in FIG. 11 is repeated each time extremely short time period T (for example. 0.1 second) elapses. Three-dimensional scanner 80 repeats acquisition and transmission of three-dimensional data in a prescribed cycle except for the prescribed case.

Then, in step S102, a controller (not shown) of three-dimensional scanner 80 determines whether or not a second operation flag has been stored in storage 508. The second operation flag is, for example, a flag indicating that the second operation is performed onto scan button 802. As described previously, the second operation onto scan button 802 is an operation for setting the multi-representation mode in display system 100. The second operation flag is stored, for example, in a prescribed storage area in three-dimensional scanner 80.

Then, in step S104, the controller of three-dimensional scanner 80 determines Whether or not the second operation has been performed onto scan button 802. When the controller of three-dimensional scanner 80 determines in step S104 that the second operation onto scan button 802 has been performed (YES in step S104), the process proceeds to step S106. When the controller of three-dimensional scanner 80 determines in step S104 that the second operation has not been performed onto scan button 802 (NO in step S104), the process proceeds to step S110.

In step S106, the controller of three-dimensional scanner 80 transmits the second operation signal as the button signal to image processing apparatus 40. Thereafter, in step S108, the controller of three-dimensional scanner 80 has the second operation flag stored in a non-volatile memory of three-dimensional scanner 80. Thereafter, the process proceeds to step S110.

In step S110, the controller of three-dimensional scanner 80 determines whether or not the first operation onto scan button 802 has been performed. The first operation onto scan button 802 during scanning is an operation to quit the scanning processing. When the controller of three-dimensional scanner 80 determines that the first operation onto scan button 802 has been performed (YES in step S110), the process ends and a non-scanning state is established.

When the controller of three-dimensional scanner 80 determines that the first operation onto scan button 802 has not been performed (NO in step S110), the process returns to step S101. In step S101, three-dimensional scanner 80 again performs image pick-up. The controller of three-dimensional scanner 80 repeatedly performs processing from step S101 to step S110 until the first operation onto scan button 802 is performed, and hence image pick-up of an object is performed each time extremely short time period T elapses.

In the example in FIG. 11, three-dimensional scanner 80 is described as performing processing in step S101 and processing from step S102 to step S108 in series. In a modification, however, three-dimensional scanner 80 may perform processing in step S101 and processing from step S102 to step S108 in parallel.

Processing in image processing apparatus 40 will now be described in step S201, acquisition unit 502 of image processing apparatus 40 acquires three-dimensional data transmitted from three-dimensional scanner 80 in step S101.

Then, in step S202, generator 504 generates single point-of-view image data based on three-dimensional data acquired in step S202. Then, in step S204, generator 504 generates multi-image data 3015 based on three-dimensional data acquired in step S201. Processing for generating single point-of-view image data in step S204 will be described with reference to FIG. 12.

Then, in step S206, controller 510 determines whether or not it has received the second operation signal. The second operation signal is the signal transmitted in step S106. When determination as YES is made in step S206, the process proceeds to step S207. When determination as NO is made in step S206, the process proceeds to step S208. In step S207, controller 510 has storage 508 store a multi-representation flag.

Then, in step S208, controller 510 determines Whether or not the multi-representation flag has been stored in storage 508. When controller 510 determines in step S208 that the multi-representation flag has been stored (YES in step S208), the process proceeds to step S212. Determination as YES is made in step S208 When image processing apparatus 40 has received the second operation signal. Controller 510 may have a representation mode immediately before turn-off of power by a user stored under last memory control, and at the time of next turn-on of power, it may take over the mode before turn-on of power for control.

When controller 510 determines in step S208 that the multi-representation flag has not been stored (NO in step S208), the process proceeds to step S214.
Determination as NO is made in step S208 when image processing apparatus 40 has not received the second operation signal.

In step S212, output unit 506 outputs multi-image data 3015 generated in step S204 to display 50. In step S214, output unit 506 outputs single point-of-view image data generated in step S202 to display 50.

Processing in display 50 will now be described. In step S302, display 50 receives image data. This image data is multi-image data 3015 transmitted in step S212 or single point-of-view image data transmitted in step S214. Then, in step S304, display 50 shows image data (multi-image data 3015 or single point-of-view image data) received in step S302. For example, when image data received in step S302 is single point-of-view image data, display 50 shows an image (single point-of-view image) in FIG. 2 based on the single point-of-view image data. When image data received in step S302 is multi-image data 3015, display 50 shows an image (multi-image) in FIG. 3 based on multi-image data 3015.

Figure 12:
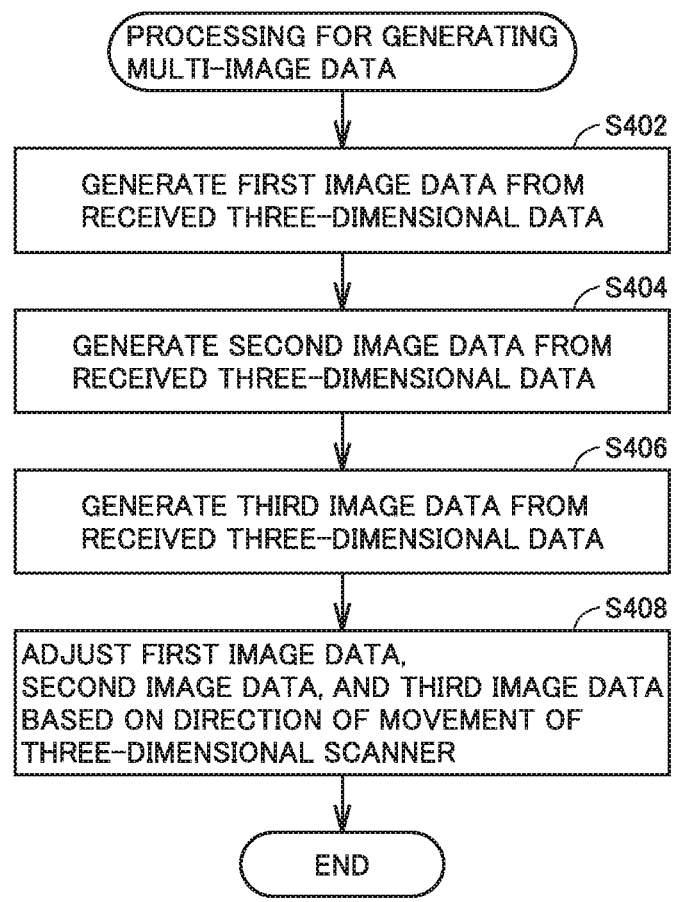
FIG. 12 is a flowchart of processing for generating multi-image data.

FIG. 12 is a flowchart of processing for generating multi-image data. Processing for generation of multi-image data by generator 504 will be described with reference to FIG. 12. As shown in FIG. 12, in step S402, first image generator 5041 generates first image data 3011 from received three-dimensional data. Then, in step S404, second image generator 5042 generates second image data. 3012 from received three-dimensional data. Then, in step S406, third image generator 5043 generates third image data 3013 from received three-dimensional data. Then, in step S408, adjuster 5050 adjusts first image data 3011, second image data 3012, and third image data 3013 based on a direction of movement of three-dimensional scanner 80 (based on the motion signal). Through processing for generating multi-image data in FIG. 12, generator 504 generates multi-image data 3015 such that second image 302 and third image 303 are shown on opposing sides of first image 301 with first image 301 being located in the center, based on a position of dentition included in each of first image 301, second image 302, and third image 303.

Figure 13:
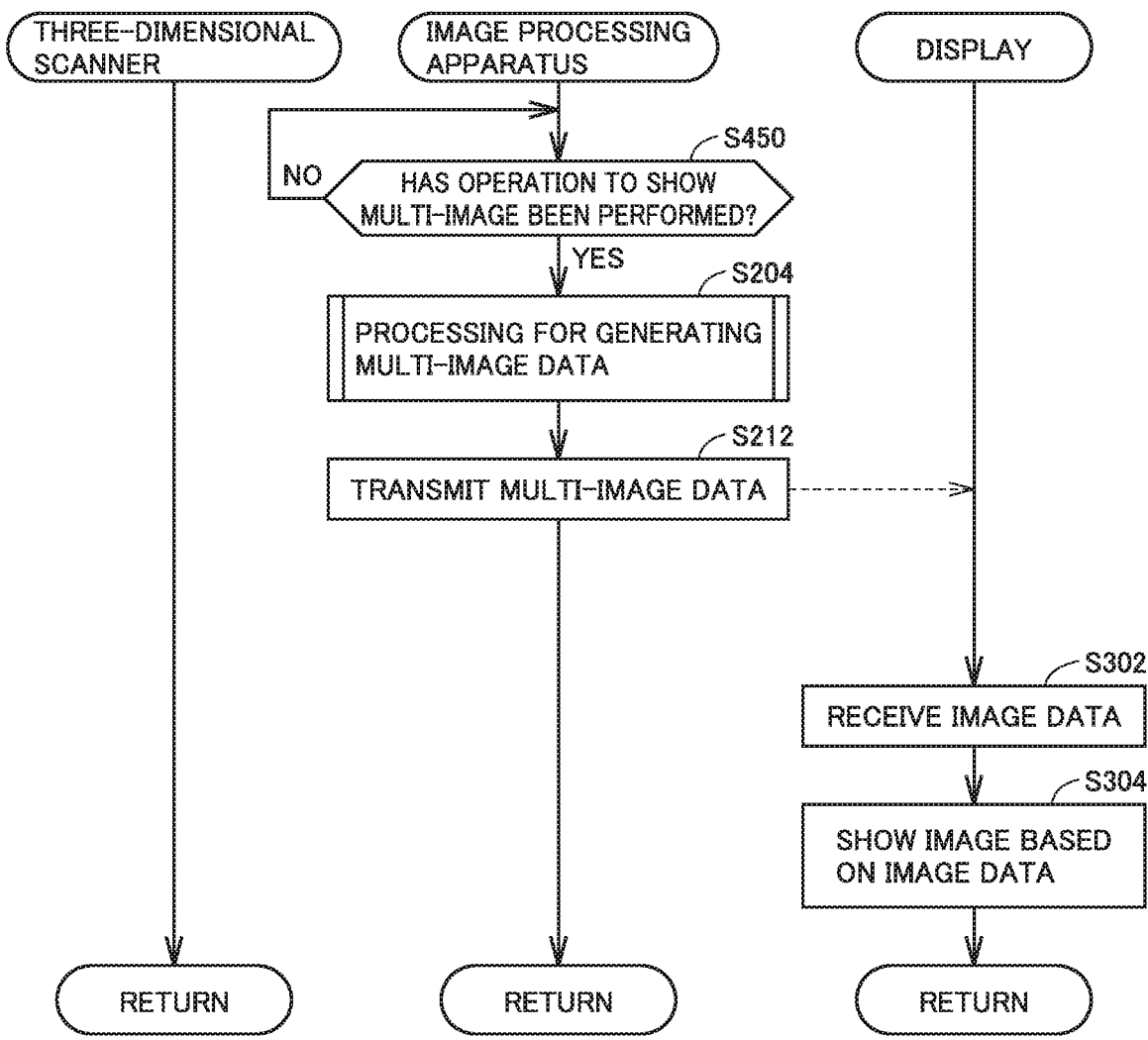
FIG. 13 is a diagram for illustrating a flowchart of the display system during non-scanning.

FIG. 13 is a diagram for illustrating a flowchart of display system 100 during non-scanning by three-dimensional scanner 80. Main processing by display system 100 during non-scanning by three-dimensional scanner 80 will be described with reference to FIG. 13. Image processing apparatus 40 determines whether or not an operation to show a multi-image has been performed. The operation for showing a multi-image is an operation, for example, performed onto a peripheral device of the image processing apparatus.

Determination processing in step S450 is repeated until image processing apparatus 40 determines that the operation for showing a multi-image has been performed. When determination as YES is made in step S450, the process proceeds to step S204. Since processing thereafter is the same as in FIG. 11, description will not be repeated.

Summary (1) Generator 504 of image processing apparatus 40 in the present embodiment generates image data of a plurality of images different in point of view toward dentition 200 based on three-dimensional data acquired by acquisition unit 502. In the present embodiment, the "plurality of images different in point of view toward dentition 200" include first image 301 in first point-of-view direction D1 toward dentition 200, second image 302 in second point-of-view direction. D2 toward dentition 200, and third image 303 in third point-of-view direction D3 toward dentition 200 as shown in FIGS. 3 and 7. Image data of the plurality of images include first image data 3011, second image data 3012, and third image data 3013.

As output unit 506 outputs image data (multi-image data 3015) of a multi-image generated by generator 504 to display 50, display 50 shows the multi-image. Therefore, a user can recognize images viewed in a plurality of directions toward dentition without rotating the shown dentition image, and consequently the user can check the image for an unscanned portion. Therefore, since the user does not have to operate an external device, the user does not have to wear gloves and to attach a disposable cover to the external device either. As set forth above, image processing apparatus 40 and display system 100 in the present embodiment can improve convenience in processing for checking of a dentition image by a user.

(2) Generator 504 generates first image data 3011 showing dentition 200 in first point-of-view direction D1, second image data 3012 showing dentition 200 in second point-of-view direction D2, and third image data 3013 showing dentition 200 in third point-of-view direction D3, as image data of a plurality of images. Adjuster 5050 in generator 504 adjusts first image data 3011, second image data 3012, and third image data 3013 such that first image 301, second image 302, and third image 303 correspond to one another in positional relation in showing first image 301 based on first image data 3011, second image 302 based on second image data 3012, and third image 303 based on third image data 3013 on display 50. Through such adjustment, display 50 can show first image 301, second image 302, and third image 303 in correspondence in positional relation with one another as shown in FIG. 3. Therefore, image processing apparatus 40 and display system 100 in the present embodiment can show first image 301, second image 302, and third image 303 to have a user recognize positional relation among first image 301, second image 302, and third image 303.

(3) In connection with positional relation in representation on display 50, adjuster 5050 adjusts first image data and second image data such that an X coordinate position or a Y coordinate position in display area 50A is identical. For example, when three-dimensional scanner 80 moves substantially in the Y-axis direction as shown in FIG. 8, adjuster 5050 makes adjustment such that Y coordinates of corresponding portions in first image 301, second image 302, and third image 303 are identical as shown in FIG. 3. Display 50 thus shows first image 301, second image 302, and third image 303 such that Y coordinates of corresponding portions in first image 301, second image 302, and third image 303 are identical. Therefore, image processing apparatus 40 and display system 100 in the present embodiment can have a user intuitively recognize positional relation among first image 301, second image 302, and third image 303. When three-dimensional scanner 80 moves substantially in the X-axis direction as shown in FIG. 8, the adjuster makes adjustment such that X coordinates of corresponding portions in first image 401, second image 402, and third image 403 are identical as shown in FIG. 8. Display 50 thus shows first image 401, second image 402, and third image 403 such that the X coordinates of corresponding portions in first image 401, second image 402, and third image 403 are identical. Therefore, image processing apparatus 40 and display system 100 in the present embodiment can have a user intuitively recognize positional relation among first image 401, second image 402, and third image 403.

(4) In the present embodiment, a manufacturer of three-dimensional scanner 80 recommends a user to set a position from which scanning by three-dimensional scanner 80 is to be started to occlusal surface 381 of rearmost molar 375. The present embodiment assumes image pick-up of occlusal surface 381 of molar 375 by a user. First image generator 5041 of generator 504 generates first image data 3011 with an initially (initial stage) obtained direction toward dentition 200 being defined as first point-of-view direction D1. Generator 504 generates second image data 3012 with a direction at a right angle or a substantially right angle with respect to the direction of dentition 200 and first point-of-view direction D1 being defined as second point-of-view direction D2, as shown in FIGS. 7 and 8. Generator 504 generates third image data 3013 with a direction opposite to second point-of-view direction D2 being defined as third point-of-view direction D3, as shown in FIGS. 7 and 8.

Therefore, display 50 can show first image 301, second image 302 in second point-of-view direction D2 at a right angle or a substantially right angle with respect to the direction of dentition 200 and first point-of-view direction D1, and third image 303 in third point-of-view direction D3 opposite to second point-of-view direction D2. Therefore, image processing apparatus 40 and display system 100 in the present embodiment can have a user recognize dentition images in first point-of-view direction D1, second point-of-view direction. D2, and third point-of-view direction D3.

(5) Generator 504 generates image data with a point of view being varied in accordance with a type of a tooth of which image is picked up by three-dimensional scanner 80. For example, when an image of molar 375 and a canine tooth is picked up by three-dimensional scanner 80, that is, when a range of image pick-up by three-dimensional scanner 80 is range α, the generator generates first image data 3011, second image data 3012, and third image data 3013 with first point-of-view direction D1 being set to the direction toward occlusal surface 381, with second point-of-view direction D2 being set to the direction toward lingual side surface 382, and with third point-of-view direction D3 being set to the direction toward buccal side surface 383. Therefore, a user can recognize an image from a point of view in accordance with a type of a tooth.

(6) For example, when image data includes image data of at least one of molar 375 and the canine tooth as shown in image G1 in FIGS. 3 and 8, first image 301 is an image from a point of view toward occlusal surface 381. Second image 302 and third image 303 are images from points of view toward side surfaces (lingual side surface 382 and buccal side surface 383). Therefore, first image 301 from the point of view toward occlusal surface 381 as well as second image 302 and third image 303 from the points of view toward the side surfaces can be shown on display 50. Therefore, a user can check whether or not there is an unscanned portion in all portions of molar 375 and the canine tooth.

(7) For example, when image data includes image data of incisor 42 as shown in image G2 in FIG. 8, first image 401 is an image from the point of view toward incisal edge 421. Second image 402 is an image from a point of view toward a side surface (lingual side surface 422 or labial side surface 423). Therefore, a user can check whether or not there is an unscanned portion in all portions of incisor 42.

(8) Acquisition unit 502 acquires three-dimensional data and a prescribed signal (the second operation signal) from three-dimensional scanner 80 as shown in FIG. 10. Generator 504 generates multi-image data 3015 based on three-dimensional data acquired at timing (step S201 in FIG. 11) substantially identical to timing (step S206 in FIG. 11) when the second operation signal has been acquired. A user can set the multi-representation mode by operating scan button 802 of three-dimensional scanner 80 without operating a peripheral device of image processing apparatus 40. Therefore, convenience of a user can be improved. In a modification, timing when image processing apparatus 40 acquires the second operation signal may be identical to timing when image processing apparatus 40 acquires three-dimensional data.

(9) Multi-image data 3015 includes image data of a part of gingiva 365 as shown in FIG. 3. Therefore, display 50 can show not only a tooth but also gingiva 365. Therefore, image processing apparatus 40 and display system 100 in the present embodiment can have a user check whether or not there is an unscanned portion not only in a tooth but also in gingiva 365.

(10) Generator 504 generates multi-image data 3015 in accordance with an amount of three-dimensional data acquired by acquisition unit 502. Consequently, first image 301, second image 302, and third image 303 are shown in accordance with an amount of acquired three-dimensional data. Therefore, a user can recognize an amount of acquired three-dimensional data.

(11) Generator 504 generates multi-image data 3015 of which three-dimensional data is sufficient. Display 50 shows a multi-image based on multi-image data 3015. Therefore, display 50 shows transparent region 316 (see FIG. 3) as a region (second missing portion) where three-dimensional data is insufficient. Therefore, image processing apparatus 40 and display system 100 in the present embodiment can have a user recognize a region where three-dimensional data is sufficient.

(12) Generator 504 generates supplemental image data that represents a portion where an amount of three-dimensional data acquired by acquisition unit 502 is smaller than a predetermined threshold value (in the present embodiment, first threshold value Th1 (D max)) in prescribed region R. Generator 504 provides supplemental image data to the first missing portion where an amount of three-dimensional data is smaller than the predetermined threshold value, and thereafter transmits multi-image data 3015 to display 50. Consequently, display 50 can show supplemental image 312 as shown in FIG. 3. Therefore, image processing apparatus 40 and display system 100 in the present embodiment can have a user recognize that three-dimensional data is slightly insufficient.

(13) When generator 504 determines that the first missing portion is in the vicinity of target tooth 360, it generates urging image data of urging image 314. Generator 504 provides urging image data to the first missing portion, and thereafter transmits multi-image data 3015 to display 50. Consequently, display 50 can show urging image 314 as shown in FIG. 3. Therefore, image processing apparatus 40 and display system 100 in the present embodiment can urge a user to scan again a portion where urging image 314 is shown.

(14) Generator 504 provides urging image data to the first missing portion in the vicinity of target tooth 360. Target tooth 360 is a tooth included in a portion designated by a user. In other words, target tooth 360 is a tooth on which a user is focusing. When three-dimensional data is missing in the vicinity of target tooth 360, the user should perform scanning again. Therefore, display 50 shows urging image 314 in the vicinity of target tooth 360 designated by the user so that the user can appropriately be urged to scan again the portion where urging image 314 is shown.

Second Embodiment

FIG. 14 shows an exemplary picture shown on display 50 in a second embodiment. In the first embodiment, as shown in FIG. 3, first image 301, second image 302, and third image 303 are equal in size in the Y-axis direction. In the second embodiment, as shown in FIG. 14, with first image 301 being located in the center, a second image 3312 which is extraction of a part of second image 302 in FIG. 3 is shown on the left thereof and a third image 3313 which is an extraction of a part of third image 303 in FIG. 3 is shown on the right of first image 301. As shown in FIG. 14, second image 3312 and third image 3313 are each an image extracted with target tooth 360 being located substantially in the center. In the second embodiment, display 50 thus shows second image 3312 of only the vicinity of target tooth 360 and third image 3313 of only the vicinity of target tooth 360. In other words, display 50 does not show the second image of a portion other than the vicinity of target tooth 360 and does not show the third image of a portion other than the vicinity of target tooth 360. The vicinity of target tooth 360 refers, for example, to an area where teeth adjacent to target tooth 360 are shown. In a modification, under the control by image processing apparatus 40, display 50 may show an area that is shown in first image 301 but is not shown in second image 3312 and third image 3313 in FIG. 14 (an area distant from target tooth 360) with visibility being lowered. "Visibility being lowered" means, for example, "lowering in image quality such as resolution and brightness."

Control in generator 504 in the second embodiment will now be described. Second image generator 5042 identifies a position of target tooth 360 designated by a user. Second image generator 5042 generates only second image data within a predetermined range U from the identified position of target tooth 360. Second image generator 5042 does not generate image data of an area out of predetermined range U. Second image data within the predetermined range corresponds to "image data within an area in the vicinity of target tooth 360."

Third image generator 5043 identifies a position of target tooth 360 designated by the user. Third image generator 5043 generates only third image data within a predetermined range from the identified position of target tooth 360. Third image generator 5043 does not generate image data of an area out of the predetermined range. Third image data within the predetermined range corresponds to "image data within an area in the vicinity of target tooth 360."

Generator 504 in the second embodiment generates second image data and third image data that represent only areas in the vicinity of a position (in the second embodiment, target tooth 360) designated by a user in first image 301. Consequently, display 50 can show second image 3312 and third image 3313 showing only areas in the vicinity of the position designated by the user in first image 301. Therefore, display 50 in the second embodiment can show only a portion in second image 3312 and third image 3313 on which the user is focusing.

According to the second embodiment, an amount of information for representation can be smaller than in an example where first image 301, second image 302, and third image 303 are shown as in the first embodiment. As set forth above, image processing apparatus 40 and display system 100 in the second embodiment can achieve lowering in loads imposed by processing for checking of a multi-image by a user.

Third Embodiment

Figure 15A:
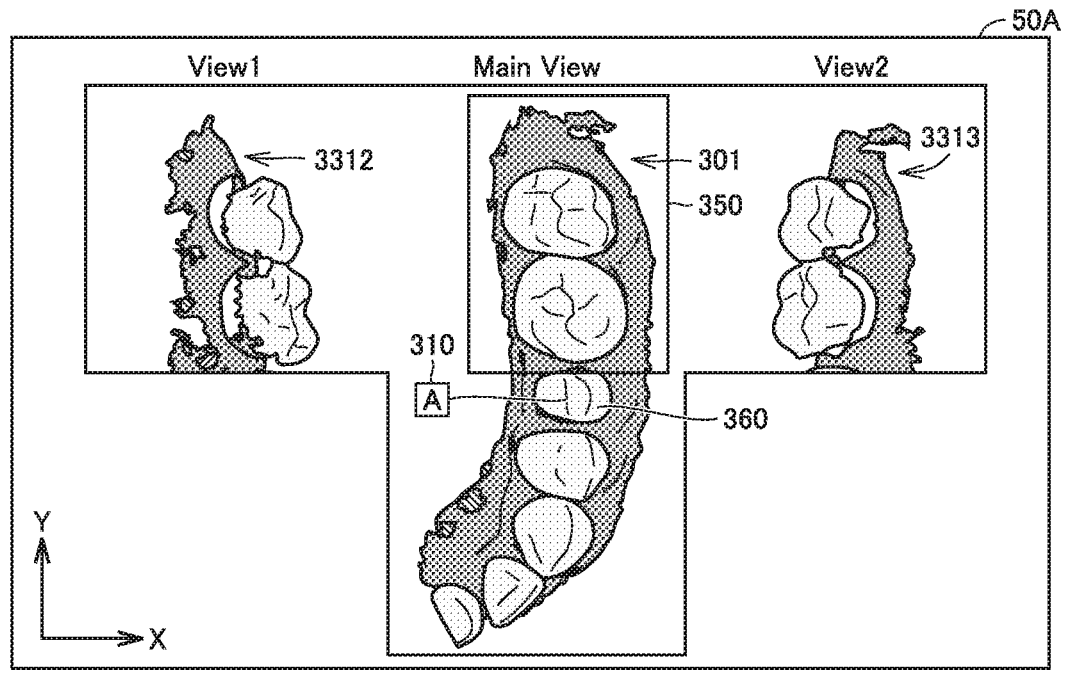
FIGS. 15A and 15B show exemplary pictures shown on the display in a third embodiment.
Figure 15B:
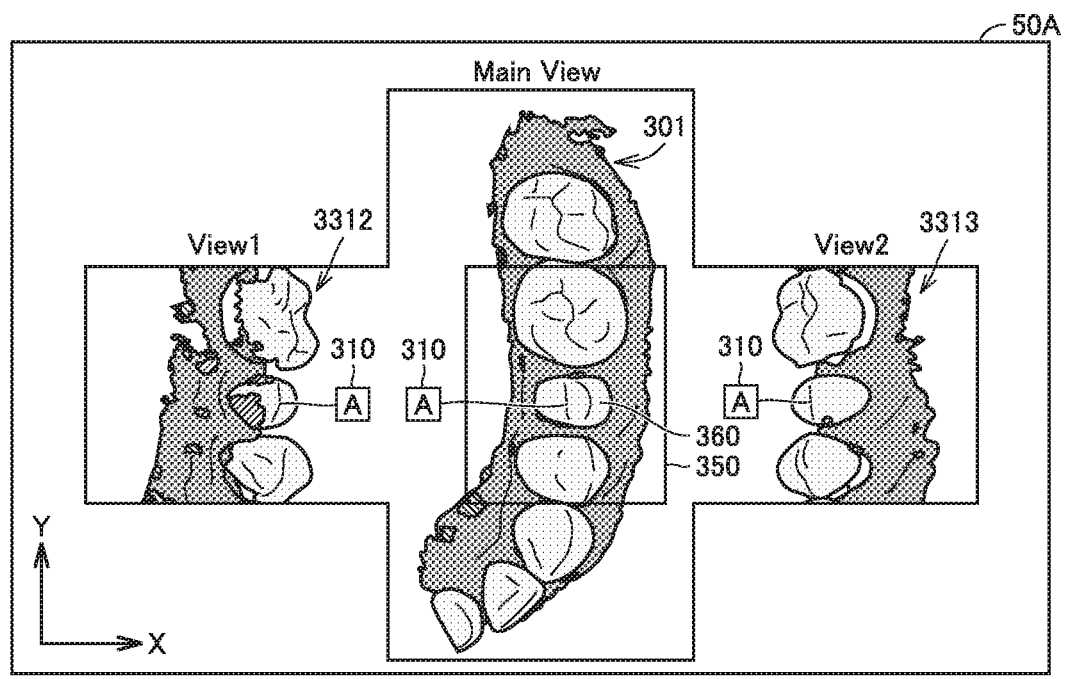

FIGS. 15A and 15B show exemplary pictures shown on display 50 in a third embodiment. Display 50 in the third embodiment shows information representing an area designated by a user. In the third embodiment, information representing an area designated by the user is described as a cursor 350. In the third embodiment, display 50 shows cursor 350 in first image 301. Display 50 shows second image 3312 and third image 3313 including only an image within cursor 350 and does not show the second image and the third image showing an image out of cursor 350.

The user can move, by moving three-dimensional scanner 80, cursor 350 within display area 50A in accordance with the movement. For example, when the user turns an end with an image pick-up surface of three-dimensional scanner 80 up, cursor 350 moves upward within display area 50A. When the user turns the end with the image pick-up surface of three-dimensional scanner 80 down, cursor 350 moves downward within display area 50A.

The example in FIG. 15A shows a state that target tooth 360 is out of cursor 350. In this state, display 50 shows second image 3312 and third image 3313 each showing a side surface and including only an image within cursor 350 in first image 301. For example, when a user desires to look at a side surface of target tooth 360, the user turns the end with the image pick-up surface of three-dimensional scanner 80 down. Then, cursor 350 moves downward within display area 50A. As shown in FIG. 15B, it is assumed that target tooth 360 is within cursor 350. In this case, display 50 shows second image 3312 and third image 3313 each showing the side surface and including only the image within cursor 350 in first image 301. The user can thus recognize second image 3312 and third image 3313 showing the side surfaces of target tooth 360.

In the third embodiment, display 50 shows second image 3312 and third image 3313 such that a Y-axis coordinate of the image within the area in first image 301 designated by the cursor and Y-axis coordinates of second image 3312 and third image 3313 are identical.

Control in generator 504 in the third embodiment will now be described. First image generator 5041 obtains a motion signal indicating a result of detection by motion sensor 804. First image generator 5041 identifies a coordinate of a designated range based on the motion signal. First image generator 5041 generates cursor data based on the identified coordinate of the designated range. First image generator 5041 generates first image data 3011 and provides cursor data to first image data 3011.

Second image generator 5042 identifies a coordinate of the designated range based on the motion signal. Second image generator 5042 extracts second image data of an area within the identified designated range from the generated second image data, and discards second image data of an area out of the identified designated range. Second image generator 5042 outputs extracted second image data to adjuster 5050. In a modification, second image generator 5042 may generate second image data of an area only within the identified designated range. Second image generator 5042 outputs generated second image data to adjuster 5050.

Third image generator 5043 identifies a coordinate of the designated range based on the motion signal. Third image generator 5043 extracts third image data of an area within the identified designated range from generated third image data and discards third image data of an area out of the identified designated range. Third image generator 5043 outputs extracted third image data to adjuster 5050. In a modification, third image generator 5043 may generate third image data of an area only within the identified designated range. Third image generator 5043 outputs generated third image data to adjuster 5050.

Then, adjuster 5050 identifies a coordinate of the designated range. Adjuster 5050 then adjusts second image data and third image data such that a Y-axis coordinate of the image within the designated range in first image 301 and Y-axis coordinates of second image 3312 and third image 3313 are identical. Adjuster 5050 transmits first image data 3011 provided with cursor data, second image data adjusted by adjuster 5050, and third image data adjusted by adjuster 5050 to display 50.

Generator 504 in the third embodiment thus generates second image data and third image data in a designated area in accordance with a result of detection by motion sensor 804. Therefore, display 50 in the third embodiment can show second image 3312 and third image 3313 within the designated range desired by a user. Therefore, convenience of the user can be improved.

Fourth Embodiment

In the first, second, and third embodiments, first point-of-view direction. D1, second point-of-view direction D2, and third point-of-view direction D3 are predetermined. Image processing apparatus 40 in the fourth embodiment includes a point-of-view input unit to which a user inputs a plurality of points of view (point-of-view directions). The user can determine a point-of-view direction by inputting a point of view to the point-of-view input unit. An exemplary point-of-view input unit will be described below.

Figure 16:
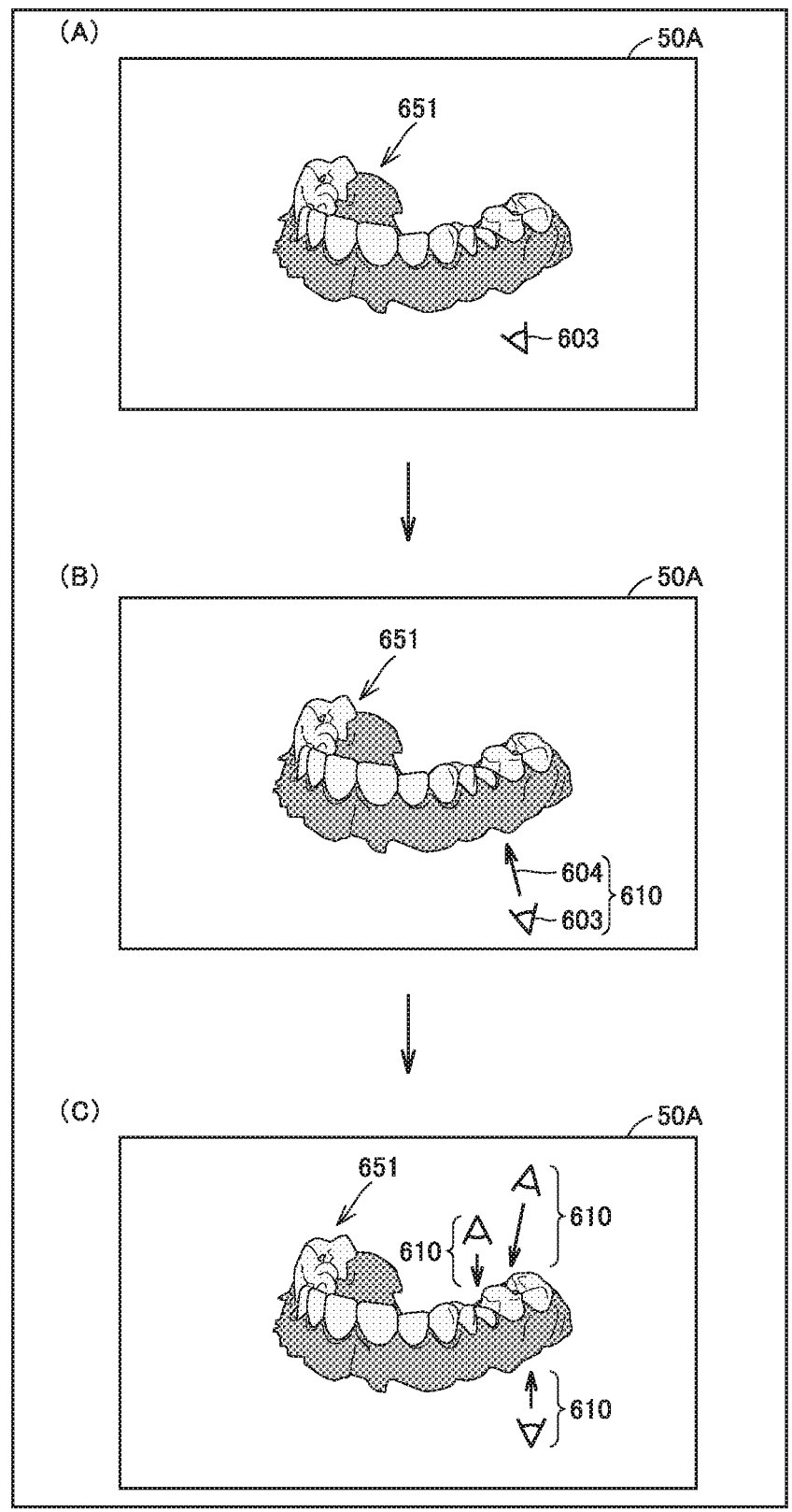
FIG. 16 shows an exemplary point-of-view direction setting picture.

A user can set a point-of-view direction setting mode by operating a peripheral device of image processing apparatus 40. When image processing apparatus 40 sets the point-of-view direction setting mode, it has display 50 show a picture for setting a point-of-view direction. FIG. 16 shows an exemplary point-of-view direction setting picture. As shown in FIG. 16 (A), display 50 three-dimensionally shows a dentition image 651. Image data of dentition image 651 is data stored in advance in memory 109 of image processing apparatus 40.

The user determines a point of view in the point-of-view direction by operating mouse 602. For example, when the user operates mouse 602 to move a pointer (not shown) within display area 50A and clicks mouse 602 at a desired location as shown in FIG. 16 (A), display 50 shows a point-of-view image 603 showing the point of view. Point-of-view image 603 is an image showing the point of view in the point-of-view direction. Thereafter, as the user performs a drag operation with mouse 602 along a desired direction within display area 50A, display 50 shows an arrow image 604 showing a point-of-view direction from point-of-view image 603 as shown in FIG. 16 (B). Point-of-view image 603 and arrow image 604 constitute a point-of-view direction image 610 for designating a point-of-view direction.

The user can set a plurality of point-of-view directions. In the example in FIG. 16 (C), three point-of-view directions are set in image processing apparatus 40. In the example in FIG. 16 (C), display 50 shows three point-of-view direction images 610. The point-of-view input unit is thus constituted of display 50 and mouse 602.

Generator 504 in the fourth embodiment generates multi-image data 3015 in accordance with a point of view input from the point-of-view input unit. Display 50 can thus show a multi-image in accordance with the point of view input by the user. Therefore, since image processing apparatus 40 in the fourth embodiment can show a multi-image in accordance with a point of view desired by a user, convenience of the user can be improved.

The point-of-view input unit described in the fourth embodiment is by way of example and a user may input a point of view according to another configuration. For example, the point-of-view input unit may receive input of an angle of a point of view from a user.

Fifth Embodiment

Some users may feel it difficult, for example, to find a point of view of the second image with respect to the first image. Image processing apparatus 40 in a fifth embodiment makes it easier for a user to find a point of view of the second image with respect to the first image. In the description of the fourth embodiment, a user can input a desired point of view through the point-of-view input unit. When the number of points of view input through the point-of-view input unit is large, the user has difficulty in visually recognizing a multi-image. Image processing apparatus 40 in the fifth embodiment allows a user to readily recognize a multi-image in spite of increase in number of points of view.

Figure 17:
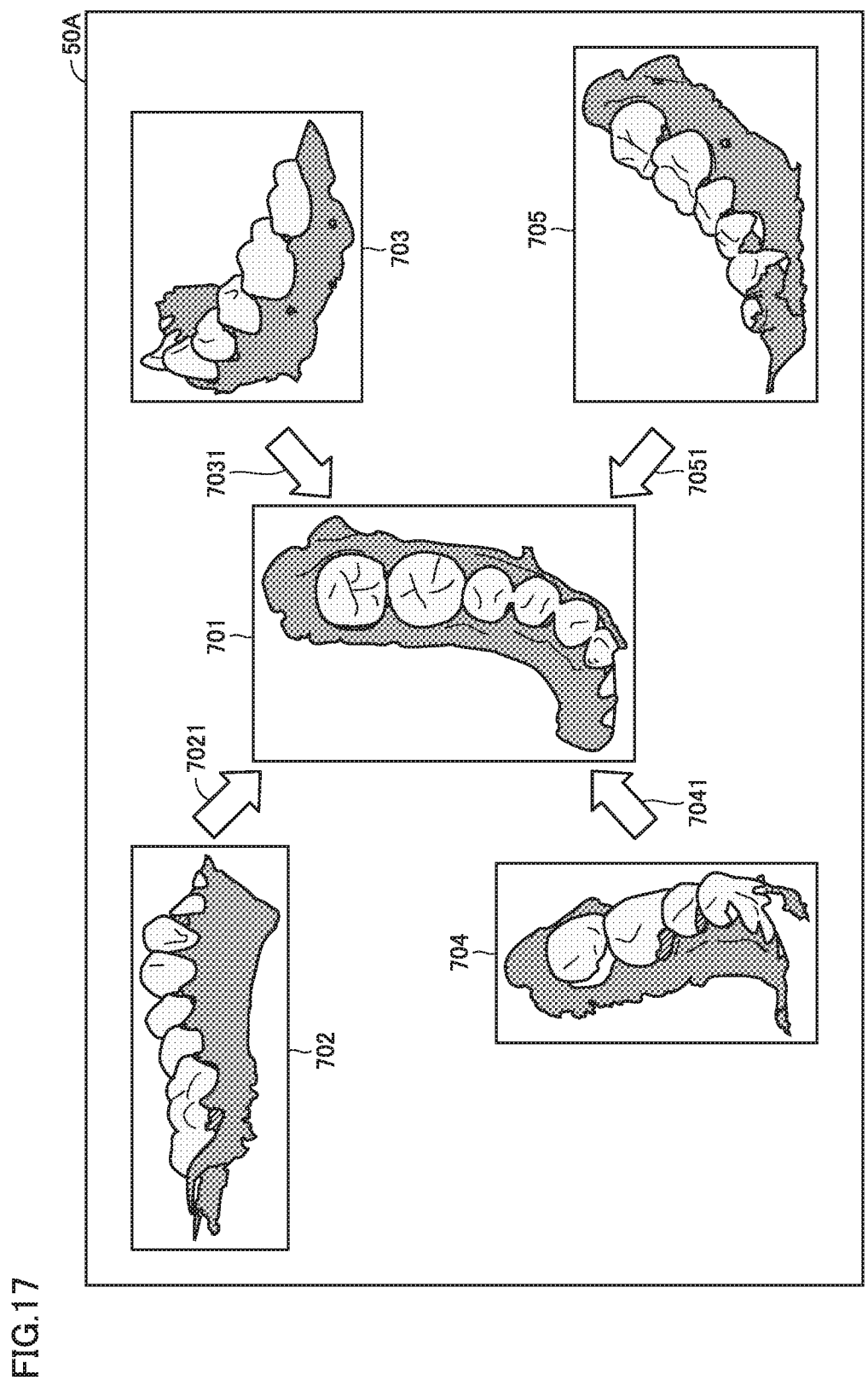
FIG. 17 shows an exemplary picture shown on the display in a fifth embodiment.

FIG. 17 shows an exemplary picture shown on display 50 in the fifth embodiment. FIG. 17 shows an example in which a user sets four points of view. Display 50 in the example in FIG. 17 shows a first image 701 in the center of display area 50A and display 50 shows a second image 702, a third image 703, a fourth image 704, and a fifth image 705. In the fifth embodiment, the number of set points of view should only be one or more and is not limited to four.

First image 701 is an image showing a right rear molar. Second image 702 is an image of dentition shown in first image 701 in a point-of-view direction from the rear toward the lingual side surface. Third image 703 is an image of dentition shown in first image 701 in a point-of-view direction from the rear toward the buccal side surface. Fourth image 704 is an image of dentition shown in first image 701 in a point-of-view direction from the front toward the lingual side surface. Fifth image 705 is an image of dentition shown in first image 701 in a point-of-view direction from the front toward the buccal side surface.

Display 50 shows a second point-of-view image 7021 between first image 701 and second image 702. Display 50 shows a third point-of-view image 7031 between first image 701 and third image 703. Display 50 shows a fourth point-of-view image 7041 between first image 701 and fourth image 704. Display 50 shows a fifth point-of-view image 7051 between first image 701 and fifth image 705.

Second point-of-view image 7021 is an arrow image showing the point-of-view direction from the rear toward the lingual side surface. Third point-of-view image 7031 is an arrow image showing the point-of-view direction from the rear toward the buccal side surface. Fourth point-of-view image 7041 is an arrow image showing the point-of-view direction from the front toward the lingual side surface. Fifth point-of-view image 7051 is an arrow image showing the point-of-view direction from the front toward the buccal side surface.

Control in generator 504 will now be described. Generator 504 in the fifth embodiment includes a fourth image generator and a fifth image generator in addition to first image generator 5041, second image generator 5042, and third image generator 5043, although they are not particularly shown. First image generator 5041 generates first image data. Second image generator 5042 generates second image data. Third image generator 5043 generates third image data. A fourth image generator 5044 generates fourth image data. A fifth image generator 5045 generates fifth image data.

First image data is image data of first image 701. Second image data is image data of second image 702. Third image data is image data of third image 703. Fourth image data is image data of fourth image 704. Fifth image data is image data of fifth image 705.

Generator 504 generates second point-of-view image data, third point-of-view image data, fourth point-of-view image data, and fifth point-of-view image data. Second point-of-view image data is image data of second point-of-view image 7021. Third point-of-view image data is image data of third point-of-view image 7031. Fourth point-of-view image data is image data of fourth point-of-view image 7041. Fifth point-of-view image data is image data of fifth point-of-view image 7051.

Adjuster 5050 adjusts first image data, second image data, third image data, fourth image data, fifth image data, second point-of-view image data, third point-of-view image data, fourth point-of-view image data, and fifth point-of-view image data such that second image 702, third image 703, fourth image 704, fifth image 705, second point-of-view image 7021, third point-of-view image 7031, fourth point-of-view image 7041, and fifth point-of-view image 7051 are shown in a manner in FIG. 17.

Generator 504 in the fifth embodiment generates point-of-view data indicating at least a point of view of second image 702 (in the fifth embodiment, second image 702, third image 703, fourth image 704, and fifth image 705) with respect to first image 701. Therefore, display 50 shows the picture as shown in FIG. 17. Therefore, image processing apparatus 40 in the fifth embodiment can allow a user to readily know at least the point of view of second image 702 with respect to first image 701.

Sixth Embodiment

In the description of the first embodiment, a user operates a peripheral device (keyboard 601 and mouse 602) before scanning to input information indicating target tooth 360 (for example, identification information (identification number) of a tooth). In a sixth embodiment, the image processing apparatus identifies a target tooth. In the sixth embodiment, an abutment tooth is defined as a target tooth. Any tooth may be defined as the target tooth, and for example, a decayed tooth may be defined as the target tooth.

For example, the image processing apparatus according to the sixth embodiment automatically identifies an abutment tooth based on three-dimensional data acquired by three-dimensional scanner 80 by using artificial intelligence (AI) of the image processing apparatus. Processing for identification of an abutment tooth by the image processing apparatus is also referred to as "identification processing."

Figure 18:
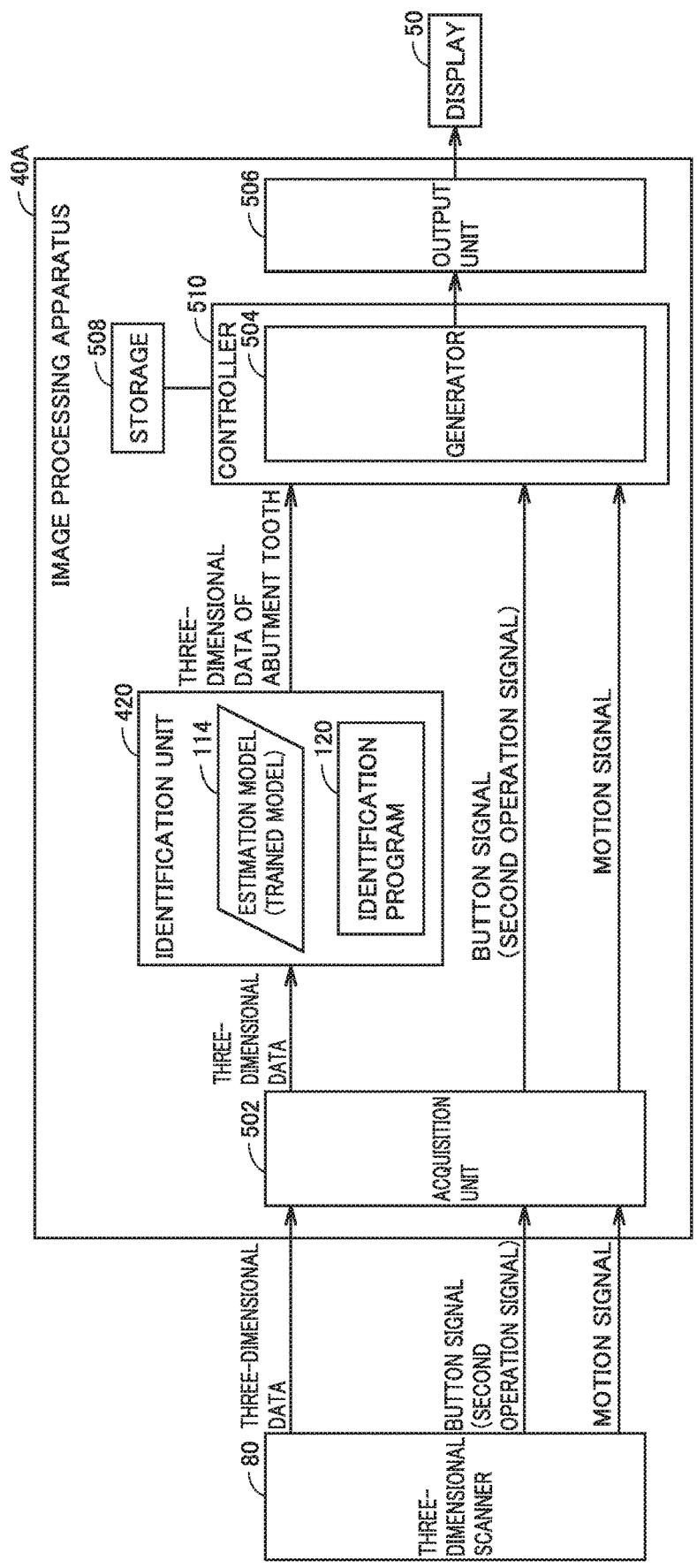
FIG. 18 is a diagram showing an exemplary functional configuration of an image processing apparatus in a sixth embodiment.

FIG. 18 is a diagram showing an exemplary functional configuration of an image processing apparatus 40A in the sixth embodiment. When image processing apparatus 40A is compared with image processing apparatus 40 in FIG. 10, they are different from each other in that image processing apparatus 40A includes an identification unit 420 whereas image processing apparatus 40 does not include identification unit 420.

Identification unit 420 includes an estimation model 114 and an identification program 120, Identification program 120 identifies an abutment tooth in dentition by using estimation model 114, based on a characteristic of a tooth corresponding to three-dimensional data acquired by acquisition unit 502. Estimation model 114 includes a neural network and a parameter of the neural network. The parameter includes a weight and a bias.

Three-dimensional data acquired by acquisition unit 502 is input to identification unit 420. The three-dimensional data corresponds to a single point-of-view image including a plurality of teeth. When identification program 120 of identification unit 420 receives three-dimensional data from acquisition unit 502, it extracts a feature value (a feature value of a plurality of teeth) included in the three-dimensional data and inputs the feature value to an input layer of the neural network. The feature value may have, for example, any value, and it may be color information of the three-dimensional data. In the neural network, for example, an intermediate layer of the neural network multiplies a value of input position information by a weight coefficient or adds a prescribed bias to the value of the input position information, and performs calculation using a prescribed function. An output layer of the neural network outputs a score representing a result of calculation in the intermediate layer. Identification program 120 identifies an abutment tooth by comparing the score and a predetermined criterion value with each other. Any approach may be employed for calculation and determination using the neural network so long as presence or absence of an abutment tooth can be identified based on three-dimensional data.

In the neural network of estimation model 114, as intermediate layers form a multi-layered structure, processing by deep learning is performed. In the sixth embodiment, for example, VoxNet, 3DShapeNets, Multi-View CNN, RotationNet, OctNet, FusionNet, PointNet, PointNet++, SSCNet, and MarrNet are used for identification program 120 for performing identification processing specializing in a three-dimensional image, however, other programs may be used. An existing scheme may be applied as a scheme of the neural network.

Training of estimation model 114 will now be described. Estimation model 114 is optimized (adjusted), for example, by learning in supervised learning using learning data. In the sixth embodiment, learning data includes a feature value of a tooth including an abutment tooth and a correct answer score (level) associated with the feature value. In training of estimation model 114, learning data is input to estimation model 114. The parameter of the neural network is updated such that the score (a result of estimation) at the time when learning data is input to estimation model 114 is closer to the correct answer score. Estimation model 114 is thus trained based on three-dimensional data including characteristics of a tooth and a result of identification (for example, a score) of a target tooth using the three-dimensional data.

When identification unit 420 identifies the abutment tooth, it outputs three-dimensional data of the abutment tooth to controller 510. Generator 504 generates first image data, second image data, and third image data based on the three-dimensional data of the abutment tooth. Consequently, display 50 can show, for example, a multi-image (first image 301, second image 302, and the third image) including the abutment tooth as shown in FIG. 3.

Identification unit 420 in the sixth embodiment can identify an abutment tooth (a tooth on which a user is focusing) and show a multi-image including the abutment tooth. Therefore, since the user does not have to input in advance information for identifying the abutment tooth, hygiene can be improved and convenience of the user can be improved. Scanning by three-dimensional scanner 80 does not have to be interrupted in order to check the abutment tooth, and a time period for scanning can be shorter.

Seventh Embodiment

FIG. 19 is a diagram for illustrating a seventh embodiment. In the seventh embodiment, display 50 can switch to any of a first representation state and a second representation state in response to an operation by a user. Examples of the operation by the user include an operation onto a peripheral device (keyboard 601 and mouse 602) of image processing apparatus 40.

FIG. 19 (A) shows a state that display 50 shows a multi-image and another content 520 (another image). Another content 520 refers to an image different from a multi-image. For example, another content includes a start button for starting prescribed control in FIG. 19 and an icon image of an application. FIG. 19 (B) shows a state that display 50 shows only a multi-image without showing another content 520.

The first representation state in FIG. 19 (A) is also a low-magnification representation state in which a multi-image is shown at a prescribed magnification. The second representation state in FIG. 19 (B) is also a high-magnification representation state in which a multi-image is shown at a magnification higher than the prescribed magnification.

According to the seventh embodiment, display 50 can switch to any of the first representation state (see FIG. 19 (A)) in which a multi-image and another content 520 are shown and the second representation state in which only images of a multi-image are shown (see FIG. 19 (B)) in response to an operation by a user. Therefore, since the user can have a desired image shown, convenience of the user can be improved.

According to the seventh embodiment, display 50 can switch to any of the low-magnification representation state (see FIG. 19 (A)) in which a multi-image is shown at a prescribed magnification and the high-magnification representation state (see FIG. 19 (B)) in which a multi-image is shown at a magnification higher than the prescribed magnification in response to an operation by a user. Therefore, since the user can have a multi-image shown at a magnification desired by the user, convenience of the user can be improved.

In a modification of the seventh embodiment, only a multi-image may be shown, with another content 520 being shown in neither of the low-magnification representation state and the high-magnification representation state. Alternatively, a multi-image and another content 520 may be shown in both of the low-magnification representation state and the high-magnification representation state. The first representation state and the second representation state may be equal to each other in magnification of an image.

Eighth Embodiment

Figure 20:
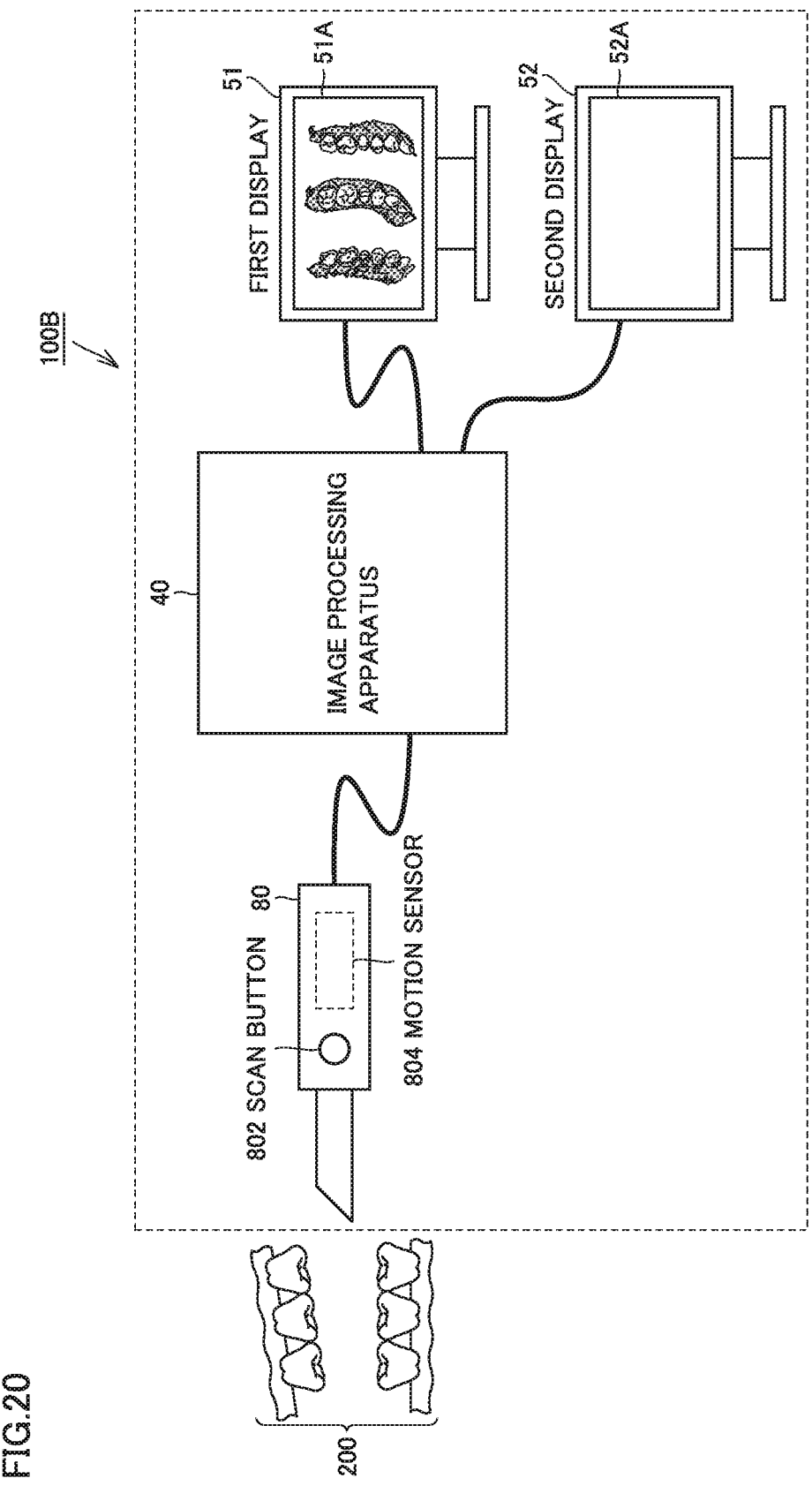
FIG. 20 is a diagram showing an exemplary configuration of a display system according to an eighth embodiment.

FIG. 20 is a diagram for illustrating an eighth embodiment. Display system 100 in the example in FIG. 1 is described as including a single display (display 50). A display system 100A in the eighth embodiment includes two displays (a first display Si. and a second display 52). First display 51 shows an image in a display area 51A. Second display 52 shows an image in a display area 52A.

Figure 21A:
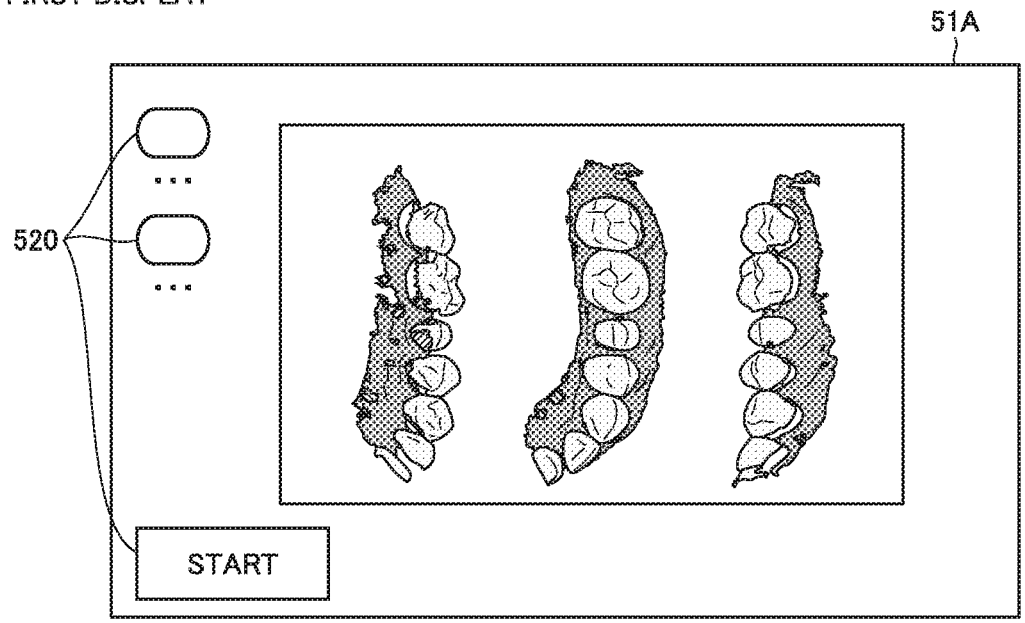
FIGS. 21A and 21B show exemplary pictures shown on the display in the eighth embodiment.
Figure 21B:
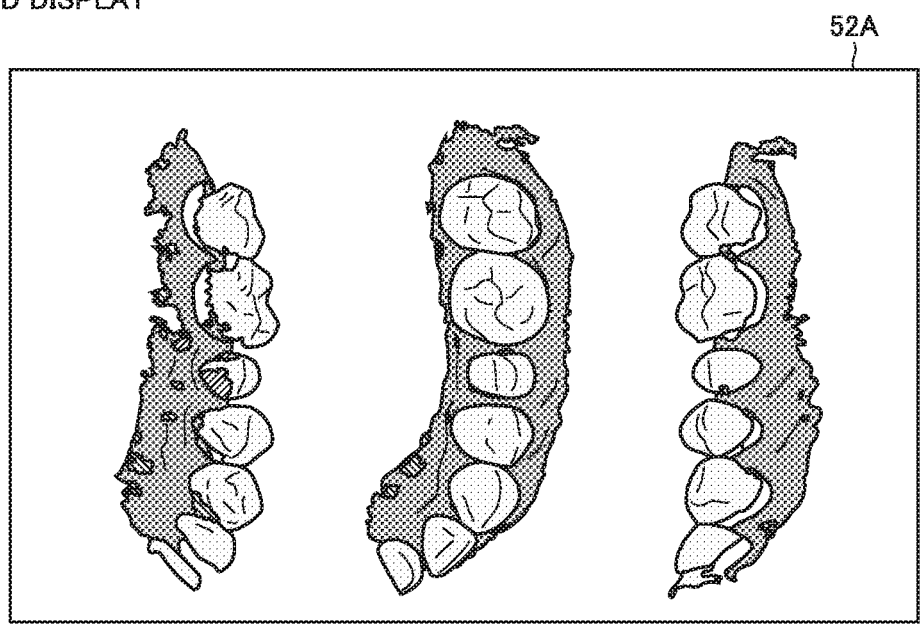

FIGS. 21A and 21B show exemplary pictures shown on first display 51 and second display 52. FIG. 21A is a diagram showing that first display 51 shows a multi-image and another content 520. FIG. 21B is a diagram showing that second display 52 shows only a multi-image without showing another content 520.

As shown in FIG. 21A, first display 51 shows a multi-image at a prescribed magnification. As shown in FIG. 21B, second display 52 shows a multi-image at a magnification higher than the prescribed magnification.

According to the eighth embodiment, first display 51 shows a multi-image and another content 520 (see FIG. 21A) whereas second display 52 shows only images of a multi-image (see FIG. 21B). Therefore, a user can have a desired image shown and hence convenience of the user can be improved.

According to the eighth embodiment, first display 51 shows a multi-image at a prescribed magnification (see FIG. 21A) whereas second display 52 shows a multi-image at a magnification higher than the prescribed magnification (see FIG. 21B). Therefore, since a user can have a multi-image shown at a magnification desired by the user, convenience of the user can be improved.

In a modification of the eighth embodiment, first display 51 and second display 52 may each show only a multi-image without showing another content 520. Alternatively, first display 51 and second display 52 may show a multi-image and another content 520. First display 51 and second display 52 may be equal to each other in magnification at which an image is shown.

Modification (1) In the embodiments described previously, acquisition unit 502 is described as acquiring three-dimensional data from three-dimensional scanner 80. Three-dimensional data, however, may be acquired from another source. For example, three-dimensional scanner 80 and image processing apparatus 40 may be connected to each other over a prescribed network. In this case, three-dimensional data is acquired from the network. Alternatively, three-dimensional data may be stored in a storage medium. In this case, three-dimensional data is acquired from a storage medium.

In the embodiments described previously, output unit 506 is described as outputting multi-image data to display 50. Output unit 506, however, may provide output to another destination. The output unit may provide output to a printer. Output unit 506 may provide output to a storage medium. In this case, the storage medium stores multi-image data. Image processing apparatus 40 and display 50 may be connected to each other over a prescribed network. In this case, output unit 506 provides output to the network.

(2) In the embodiments described previously, a portion of which image is picked up first (initially) by three-dimensional scanner 80 is assumed as occlusal surface 381 of molar 375. Image processing apparatus 40, however, may identify occlusal surface 381 of molar 375.

In general, an end of a molar (a part of a tooth opposite to gingiva) is larger in area of a region having a color of a tooth than an end of another tooth. The color of the tooth is referred to as white below. In other words, at a coordinate (for example, a Z coordinate) indicating the end of the molar, the molar is larger in area of a white region than another tooth.

In the present modification, generator 504 extracts three-dimensional data of Which Z coordinate belongs to a predetermined Z coordinate range, from three-dimensional data acquired by acquisition unit 502. Generator 504 then determines whether or not an amount of three-dimensional data representing the white color in the extracted three-dimensional data is equal to or larger than a predetermined threshold value. The amount of three-dimensional data representing the white color being equal to or larger than the predetermined threshold value means that a portion corresponding to the three-dimensional data is highly likely occlusal surface 381 of molar 375. When generator 504 determines that the amount of three-dimensional data representing the white color is equal to or larger than the threshold value, it determines that three-dimensional data from which the three-dimensional data has been extracted is three-dimensional data of occlusal surface 381. When generator 504 determines that the amount of three-dimensional data representing the white color is smaller than the threshold value, it determines that three-dimensional data from which the three-dimensional data has been extracted is three-dimensional data of a portion other than occlusal surface 381.

With the approach above, generator 504 may determine Whether or not three-dimensional data acquired by acquisition unit 502 is three-dimensional data representing occlusal surface 381.

Alternatively, generator 504 may identify occlusal surface 381 by using another approach. For example, occlusal surface 381 may be identified by using the AI described in the sixth embodiment.

(3) In the embodiments described previously, display 50 is described as showing at least three images (first image 301, second image 302, and third image 303). The number of images shown on display 50, however, may be set to "two" or "four" or more. For example, display 50 may show first image 301 and second image 302.

(4) The display system in the embodiments described previously is described as being able to switching between representation of a single point-of-view image and representation of a multi-image. The display system, however, may show a multi-image without showing a single point-of-view image.

(5) At least a part of processing by the image processing apparatus described previously may be performed by another apparatus. Examples of another apparatus may include at least one of the three-dimensional scanner and the display.

(6) In the embodiments described previously, the image processing apparatus is described as setting the single point-of-view representation mode before the second operation onto scan button 802 is performed and setting the multi-representation mode when the second operation onto scan button 802 is performed. For example, however, such a configuration that the image processing apparatus sets the multi-representation mode while an operation by a user is continued (for example, the operation onto scan button 802 is continued by the user) may be adopted. The image processing apparatus that adopts the configuration sets the single point-of-view representation mode during a period other than a period during which the operation by the user is continued.

(7) In the embodiments described previously, adjuster 5050 is described as adjusting first image data, second image data, and third image data. Adjustment processing by adjuster 5050, however, does not have to be performed. According to such a configuration, loads imposed by adjustment processing by adjuster 5050 can be reduced.

(8) In the embodiments described previously, all images in a multi-image (first image 301, second image 302, and third image 303) shown on display 50 are described as being two-dimensional. At least one image in a multi-image shown on display 50, however, may be shown as a single point-of-view image.

(9) In the example in FIG. 11, generator 504 is described as generating multi-image data on condition that acquisition unit 502 has acquired three-dimensional data (step S201 and step S204 in FIG. 11). Another condition, however, may be adopted as the condition for generator 504 to generate multi-image data. For example, a condition that the second operation signal is received may be defined as the condition.

(10) In the second embodiment, image processing apparatus 40 is described as having display 50 show second image 3312 of only the vicinity of target tooth 360 and third image 3313 of only the vicinity of target tooth 360 as shown in FIG. 14. In a modification, even though a user has not designated target tooth 360, under the control by image processing apparatus 40, display 50 may show, with first image 301 being located in the center as shown in FIG. 14, second image 3312 which is extraction of a part of second image 302 on the left of first image 301 and show third image 3313 which is extraction of a part of third image 303 in FIG. 3 on the right of first image 301. Such representation is referred to as "extracted representation" below.

According to the present modification, even though a user has not designated target tooth 360, image processing apparatus 40 can have a tooth that is being scanned shown in a substantially central portion of display area 50A by performing extracted representation. Consequently, the user can recognize that the tooth shown in the substantially central portion of display area 50A is being scanned.

Furthermore, during scanning, image processing apparatus 40 may perform extracted representation, and when a user performs the first operation to stop scanning, the image processing apparatus may have display 50 perform extracted representation of target tooth 360 designated subsequently by the user. Such identification includes, for example, identification based on designation by a user and identification by image processing apparatus 40 with the use of an AI function. The user can thus smoothly have a desired range of a dental arch scanned and subsequently can check a status of scanning of only target tooth 360 which should completely be scanned.

(11) Image processing apparatus 40 may adopt a configuration for showing second image 3312 and third image 3313 (see FIG. 14) on display 50 as being enlarged at a prescribed magnification. When such a configuration is adopted, image processing apparatus 40 generates multi-image data 3015 such that a position of the center in the X-axis direction or the Y-axis direction of target tooth 360 is identical or substantially identical among first image 301, second image 3312, and third image 3313. As display 50 shows images based on multi-image data 3015, images (second image 3312 and third image 3313) of side surfaces of dentition can be shown as being enlarged. Therefore, a user can readily check a side surface of important target tooth 360 which does not tend to completely be scanned. A user may be able to set a prescribed magnification.

At least one of the embodiments described previously and the modifications may be applied to any of the embodiments described previously and the modifications.

Though embodiments of the present invention have been described, it should be understood that the embodiments disclosed herein are illustrative and non-restrictive in every respect. The scope of the present invention is defined by the terms of the claims and is intended to include any modifications within the scope and meaning equivalent to the terms of the claims.

What is claimed is:

1. An image processing apparatus comprising:
   an acquisition unit that acquires three-dimensional data of dentition including a plurality of teeth in an oral cavity;
   a generator that generates image data of a plurality of images different in point of view toward the dentition based on the three-dimensional data acquired by the acquisition unit; and
   an output unit that outputs to a display, the image data generated by the generator,
   wherein the generator
      generates, as the image data of the plurality of images, first image data representing the dentition in a first point-of-view direction toward an incisal edge of an incisor tooth or an occlusal surface of molar in the oral cavity, second image data representing the dentition in a second point-of-view direction toward a lingual side surface in the oral cavity forming a positive angle of predetermined degrees with the first point-of-view direction, and third image data representing the dentition in a third point-of-view direction toward a labial side surface in the oral cavity forming a negative angle of the predetermined degrees with the first point-of-view direction, and
      adjusts the first image data, the second image data, and the third image data such that a second image based on the second image data and a third image based on the third image data are located on respective opposing sides of a first image based on the first image data, and such that the first image, the second image, and the third image correspond to each other in positional relation on the display.

2. The image processing apparatus according to claim 1, wherein the generator adjusts the first image data and the second image data such that any one of an X coordinate position and a Y coordinate position in a display area of the display is identical or substantially identical.

3. The image processing apparatus according to claim 1, wherein the generator generates the second image data that represents only a region in the first image near a position designated by a user.

4. The image processing apparatus according to claim 1, wherein when the image data includes image data of at least one of a molar and a canine tooth, the first image is an image from a point of view toward an occlusal surface and the second image is an image from a point of view toward a side surface.

5. The image processing apparatus according to claim 1, wherein when the image data includes image data of an incisor, the first image is an image from a point of view toward an incisal edge and the second image is an image from a point of view toward a side surface.

6. The image processing apparatus according to claim 1, wherein the generator generates point-of-view data that represents a point of view of the second image with respect to the first image.

7. The image processing apparatus according to claim 1, wherein
   the acquisition unit acquires the three-dimensional data from a three-dimensional scanner, the three-dimensional scanner includes a sensor that detects an operation onto the three-dimensional scanner by a user, and
   the generator generates the second image data of a designated region in accordance with a result of detection by the sensor.

8. The image processing apparatus according to claim 1, wherein
   the acquisition unit acquires the three-dimensional data and a prescribed signal from a three-dimensional scanner, and
   the generator generates the image data of the plurality of images based on the three-dimensional data acquired at timing identical or substantially identical to timing of acquisition of the prescribed signal.

9. The image processing apparatus according to claim 1, wherein
   the generator generates the image data with a point of view being varied in accordance with a type of a tooth.

10. The image processing apparatus according to claim 1, wherein the image data includes image data of a part of gingiva.

11. The image processing apparatus according to claim 1, wherein the generator generates the image data of the plurality of images in accordance with an amount of the three-dimensional data acquired by the acquisition unit.

12. The image processing apparatus according to claim 11, wherein the generator generates the image data of the plurality of images of only a portion where the three-dimensional data is sufficient.

13. The image processing apparatus according to claim 11, wherein the generator provides first additional data to a portion where an amount of the three-dimensional data is smaller than a predetermined threshold value in a prescribed region.

14. The image processing apparatus according to claim 11, wherein the generator provides second additional data to a portion that a user is urged to scan again.

15. The image processing apparatus according to claim 14, wherein the portion is included in a portion designated by the user.

16. The image processing apparatus according to claim 1, further comprising
an identification unit that identifies a target tooth in the dentition by using an estimation model including a neural network based on a characteristic of a tooth corresponding to the three-dimensional data acquired by the acquisition unit,
wherein the estimation model is trained based on the three-dimensional data including the characteristic of the tooth and a result of identification of the target tooth based on the three-dimensional data.

17. The image processing apparatus according to claim 16, wherein the target tooth is an abutment tooth.

18. The image processing apparatus according to claim 1, further comprising
a point-of-view input unit to which a plurality of points of view are input by a user,
wherein the generator generates the image data in accordance with the plurality of points of view input to the point-of-view input unit.

19. A display system comprising:
a three-dimensional scanner that generates three-dimensional data of dentition including a plurality of teeth in an oral cavity;
an image processing apparatus; and
a display,
the image processing apparatus including
an acquisition unit that acquires the three-dimensional data from the three-dimensional scanner,
a generator that generates image data of a plurality of images different in point of view toward the dentition based on the three-dimensional data acquired by the acquisition unit, and
an output unit that outputs the image data generated by the generator to the display, the display showing the plurality of images based on the image data output from the output unit,
wherein the generator
generates, as the image data of the plurality of images, first image data representing the dentition in a first point-of-view direction toward an incisal edge of an incisor tooth or an occlusal surface of molar in the oral cavity, second image data representing the dentition in a second point-of-view direction toward a lingual side surface in the oral cavity forming a positive angle of predetermined degrees with the first point-of-view direction, and third image data representing the dentition in a third point-of-view direction toward a labial side surface in the oral cavity forming a negative angle of the predetermined degrees with the first point-of-view direction, and
adjusts the first image data, the second image data, and the third image data such that a second image based on the second image data and a third image based on the third image data are located on respective opposing sides of a first image based on the first image data, and such that the first image, the second image, and the third image correspond to each other in positional relation on the display.

20. The display system according to claim 19, wherein the display can switch between a first representation state in which the plurality of images and another content are shown and a second representation state in which only the plurality of images are shown.

21. The display system according to claim 19, wherein the display includes a first display that shows the plurality of images and another content and a second display that shows only the plurality of images.

22. The display system according to claim 19, wherein the display can switch between a low-magnification representation state in which the plurality of images are shown at a prescribed magnification and a high-magnification representation state in which the plurality of images are shown at a magnification higher than the prescribed magnification.

23. The display system according to claim 19, wherein the display includes a first display that shows the plurality of images at a prescribed magnification and a second display that shows the plurality of images at a magnification higher than the prescribed magnification.

24. An image processing method comprising:
acquiring three-dimensional data of dentition including a plurality of teeth in an oral cavity;
generating image data of a plurality of images different in point of view toward the dentition based on the acquired three-dimensional data; and
outputting the generated image data to a display,
wherein generating the image data including
generating, as the image data of the plurality of images, first image data representing the dentition in a first point-of-view direction toward an incisal edge of an incisor tooth or an occlusal surface of molar in the oral cavity, second image data representing the dentition in a second point-of-view direction toward a lingual side surface in the oral cavity forming a positive angle of predetermined degrees with the first point-of-view direction, and third image data representing the dentition in a third point-of-view direction toward a labial side surface in the oral cavity forming a negative angle of the predetermined degrees with the first point-of-view direction, and
adjusting the first image data, the second image data, and the third image data such that a second image based on the second image data and a third image based on the third image data are located on respective opposing sides of a first image based on the first image data, and such that the first image, the second image, and the third image correspond to each other in positional relation on the display.

25. A computer readable storage medium that stores a program, the program causing a computer to perform:
acquiring three-dimensional data of dentition including a plurality of teeth in an oral cavity;
generating image data of a plurality of images different in point of view toward the dentition based on the acquired three-dimensional data; and
outputting the generated image data to a display,
wherein generating the image data including
generating, as the image data of the plurality of images, first image data representing the dentition in a first point-of-view direction toward an incisal edge of an incisor tooth or an occlusal surface of molar in the oral cavity, second image data representing the dentition in a second point-of-view direction toward a lingual side surface in the oral cavity forming a positive angle of predetermined degrees with the first point-of-view direction, and third image data representing the dentition in a third point-of-view direction toward a labial side surface in the oral cavity forming a negative angle of the predetermined degrees with the first point-of-view direction, and adjusting the first image data, the second image data, and the third image data such that a second image based on the second image data and a third image based on the third image data are located on respective opposing sides of a first image based on the first image data, and such that the first image, the second image, and the third image correspond to each other in positional relation on the display.

26. The image processing apparatus according to claim 1, wherein the predetermined degrees include at least one of 90 degrees, approximately 90 degrees, 45 degrees, approximately 45 degrees, 30 degrees, and approximately 30 degrees.

27. The image processing apparatus according to claim 1, wherein the acquisition unit acquires the three-dimensional data from a three-dimensional scanner, and the generator generates, during scanning by the three-dimensional scanner, the first image data, the second image data, and the third image data for teeth to which an image pick-up surface of the three-dimensional scanner directed.

\* \* \* \* \*